(12) United States Patent
Iiams et al.

(10) Patent No.: US 8,165,824 B2
(45) Date of Patent: Apr. 24, 2012

(54) DETECTING ENVIRONMENTAL INTERFERENT IN A TRANSDERMAL ALCOHOL MONITOR

(75) Inventors: Michael Leonard Iiams, Littleton, CO (US); Ben Franklin Houston, Denver, CO (US); Royce Alan McDonald, Northglenn, CO (US); Jeffrey Scott Hawthorne, Bennett, CO (US); Mark Henry Wojcik, Littleton, CO (US); Gordon William Murray, Lone Tree, CO (US); Charles Thomas Champion, Denver, CO (US)

(73) Assignee: Alcohol Monitoring Systems, Inc., Littleton, CO (US)

( * ) Notice: Subject to any disclaimer, the term of this patent is extended or adjusted under 35 U.S.C. 154(b) by 362 days.

(21) Appl. No.: 12/503,067

(22) Filed: Jul. 14, 2009

(65) Prior Publication Data

US 2011/0015873 A1 Jan. 20, 2011

(51) Int. Cl.
*G01N 31/00* (2006.01)
*A61B 5/00* (2006.01)

(52) U.S. Cl. ............................ 702/24; 600/300; 600/301
(58) Field of Classification Search .................... 702/24; 600/300, 301; 340/573.1
See application file for complete search history.

(56) References Cited

U.S. PATENT DOCUMENTS

| | | | | |
|---|---|---|---|---|
| 5,048,321 | A | 9/1991 | Chow | .............................. 73/23.3 |
| 5,612,896 | A | 3/1997 | Stock | ............................. 364/497 |
| 2006/0202836 | A1 | 9/2006 | Hawthorne et al. | ........ 340/573.1 |
| 2006/0202837 | A1 * | 9/2006 | Hawthorne et al. | ........ 340/573.1 |
| 2007/0073118 | A1 | 3/2007 | Ridder et al. | .................. 600/322 |
| 2009/0182216 | A1 * | 7/2009 | Roushey et al. | .............. 600/364 |

OTHER PUBLICATIONS

Joseph T. Sakai et al.; Validity of Transdermal Alcohol Monitoring: Fixed and Self-Regulated Dosing; Jan. 2006; Alcoholism: Clinical and Experimental Research, vol. 30, No. 1, pp. 26-33.

Lee W. Young, Notification of Transmittal of the International Search Report and the Written Opinion of the International Searching Authority, or the Declaration; Aug. 31, 2010.

* cited by examiner

*Primary Examiner* — Bryan Bui
(74) *Attorney, Agent, or Firm* — Stanley J. Gradisar Attorney at Law LLC; Stanley J. Gradisar

(57) ABSTRACT

An improvement in monitoring alcohol levels through transdermal testing is provided by detecting if environmental gasses, referred to as interferents, have been introduced into a transdermal vapor sample. An insensible skin perspiration sample may not be completely controlled and can contain interferents from an environmental source rather than the subject. Before testing a skin perspiration sample, the alcohol sensor is sampled and averaged to establish a baseline value. A sample is drawn and presented to the alcohol sensor. The output of the alcohol sensor is monitored to determine the amount of alcohol in the sample. A maximum alcohol sensor value for the transdermal alcohol monitor is set by determining the baseline value when no alcohol is present in the sample. Subsequent baseline values during a reading above the maximum alcohol sensor value indicate that an environmental interferent is present in the alcohol sensor.

36 Claims, 18 Drawing Sheets

DETECTING ENVIRONMENTAL INTERFERENT IN A TRANSDERMAL ALCOHOL MONITOR

CROSS-REFERENCES TO RELATED APPLICATIONS

This application is related to a application Ser. No. 12/013,931 filed on Jan. 14, 2008 titled "Moisture Control In A Transdermal Blood Alcohol Monitor" owned by the same assignee of this invention, and to application Ser. No. 10/441,940 Titled "Method And Apparatus For Remote Blood Alcohol Monitoring" filed on May 19, 2003, now U.S. Pat. No. 7,462,149, and owned by the same assignee of this invention, which are incorporated herein by reference in their entirety for all that is taught and disclosed therein.

FIELD OF THE INVENTION

The invention relates to transdermal alcohol monitoring and methods of determining an environmental interferent within a transdermal alcohol concentration reading.

BACKGROUND

Individuals on probation, parole, or in alcohol treatment programs may be prohibited from consuming alcohol, and many federal, state, and local law enforcement agencies require testing to ensure participants in court ordered programs remain alcohol free. As alcohol is ingested orally, it is absorbed into the body's blood and distributed throughout the body via the circulatory system. Alcohol is eliminated from the body by two mechanisms: metabolism and excretion. Metabolism accounts for the removal of greater than 90% of the alcohol consumed, removing it from the body via oxidation of the ethyl alcohol molecule to carbon dioxide and water primarily in the liver. The remaining alcohol is excreted unchanged wherever water is removed from the body— breath, urine, insensible skin perspiration, and saliva. Although excretion accounts for less than 10% of the eliminated alcohol, it is significant because unaltered alcohol excretion permits an accurate measurement of alcohol concentration in the body by way of both breath analysis and insensible skin perspiration. Insensible skin perspiration is the vapor that escapes through the skin through sweating. The average person will emit approximately one liter of insensible skin perspiration each day. This insensible skin perspiration can be used to obtain a transdermal measurement estimating a blood alcohol concentration, referred to as Transdermal Alcohol Concentration ("TAC").

Transdermal monitoring of alcohol levels is accomplished by taking measurements of alcohol contained in the insensible skin perspiration that is expelled transdermally through human skin. Throughout this description of the invention, insensible skin perspiration may be referred to as "vapor," "air vapor," "air vapor sample," "air vapor volume," "sample," "sample volume," "air sample" "transdermal vapor sample," and "air sample volume," interchangeably, with no difference in meaning intended. A monitoring device in the form of a bracelet that is worn on the ankle or arm of the subject captures the air vapor released from the skin under the bracelet and measures the alcohol contained therein, if any.

There are numerous advantages to transdermal alcohol monitoring, as opposed to breath-testing, including, but not limited to, the ability to take readings at any time without the knowledge of the subject, consistent and continuous testing (unlike breath alcohol testing where a subject breathing incorrectly into the testing device can cause inaccurate results), and the ability to convert such readings into electrical signals that can be transmitted to a central monitoring station.

The transdermal alcohol monitor described in co-pending application Ser. No. 12/013,931 better manages the build-up of moisture within a transdermal blood alcohol monitor to prevent damage to the various internal components, and to increase the service life of the transdermal alcohol monitor.

Regarding fixed-location breath-testing devices, a fuel cell is subjected to a breath sample having an alcohol vapor component. The physical measurement variable $i(t)$, which is obtained by the electrochemical conversion, is supplied to an evaluation circuit which determines a measurement value proportional to the alcohol vapor concentration. The measurement value is determined by integrating the signal trace of the physical measurement value as a function of time $(t)$. A sample curve of such a signal trace from a transdermal alcohol monitor is shown in FIG. 2. When the measuring cell is charged with alcohol vapor, the measurement signal first increases starting from a reference value, passes through a maximum value, and returns again to a minimum value in the vicinity of the reference value after the complete electrochemical conversion. The area enclosed between the function value of the measurement signal and the reference value is proportional to the concentration of the alcohol vapor in the breath sample. By looking at different sections of the area under the curve these methods determine different types of interferents in the breath sample that is being analyzed. An interferent may be defined as any substance whose presence interferes with the sample being measured and generates incorrect results. Thus, by utilizing the above techniques, true alcohol readings can be distinguished from the interferent readings.

However, these methods will not work with transdermal alcohol monitoring, as the interferent is different than in a breath test. The interferents in transdermal testing are of a significantly different concentration than a typical transdermal alcohol sample obtained from the skin. Interferents in transdermal testing will typically create a much different sample curve entirely and can thus be readily identified. However, occasionally, the concentration of the interferent is low enough to not create a completely different sample curve. In such cases, the interferent sampled in transdermal testing can generate a sample curve that looks very similar to a drinking event. Therefore a new method of detecting interferents in transdermal alcohol monitoring is needed.

SUMMARY

This Summary is provided to introduce in a simplified form a selection of concepts that are further described below in the Detailed Description. This Summary is not intended to identify key features or essential features of the claimed subject matter, nor is it intended to be used to limit the scope of the claimed subject matter.

An objective of this invention is to improve the monitoring of alcohol levels in a subject through transdermal testing by providing a way to detect if environmental gases, referred to as interferents, have been introduced into a transdermal vapor sample. The reason that this is important is that with transdermal testing, utilizing an alcohol monitor of the type described in application Ser. No. 12/013,931 referenced above, the insensible skin perspiration sample is not completely controlled and can contain interferents from an environmental source rather than entirely coming from the skin of the subject being monitored. This is due to the fact that the exhaust vent from the fuel cell allows environmental interferents to backflow into the fuel cell. Before testing a sample from the skin of the subject, the output from the alcohol sensor is sampled and averaged to establish a baseline, or offset, or zero level reading, hereinafter referred to as the baseline value or offset value. The pump in the transdermal alcohol monitor is then activated, and a sample is drawn from the sample collection chamber and presented to the fuel cell. The output of the alcohol sensor is then monitored to determine the amount of alcohol in the sample. By monitoring the baseline value prior to the sample being introduced to the fuel cell compared to a maximum fuel cell voltage value for the transdermal alcohol monitor, a determination is made if an environmental interferent is present in the fuel cell.

DETAILED DESCRIPTION

Figure 1:
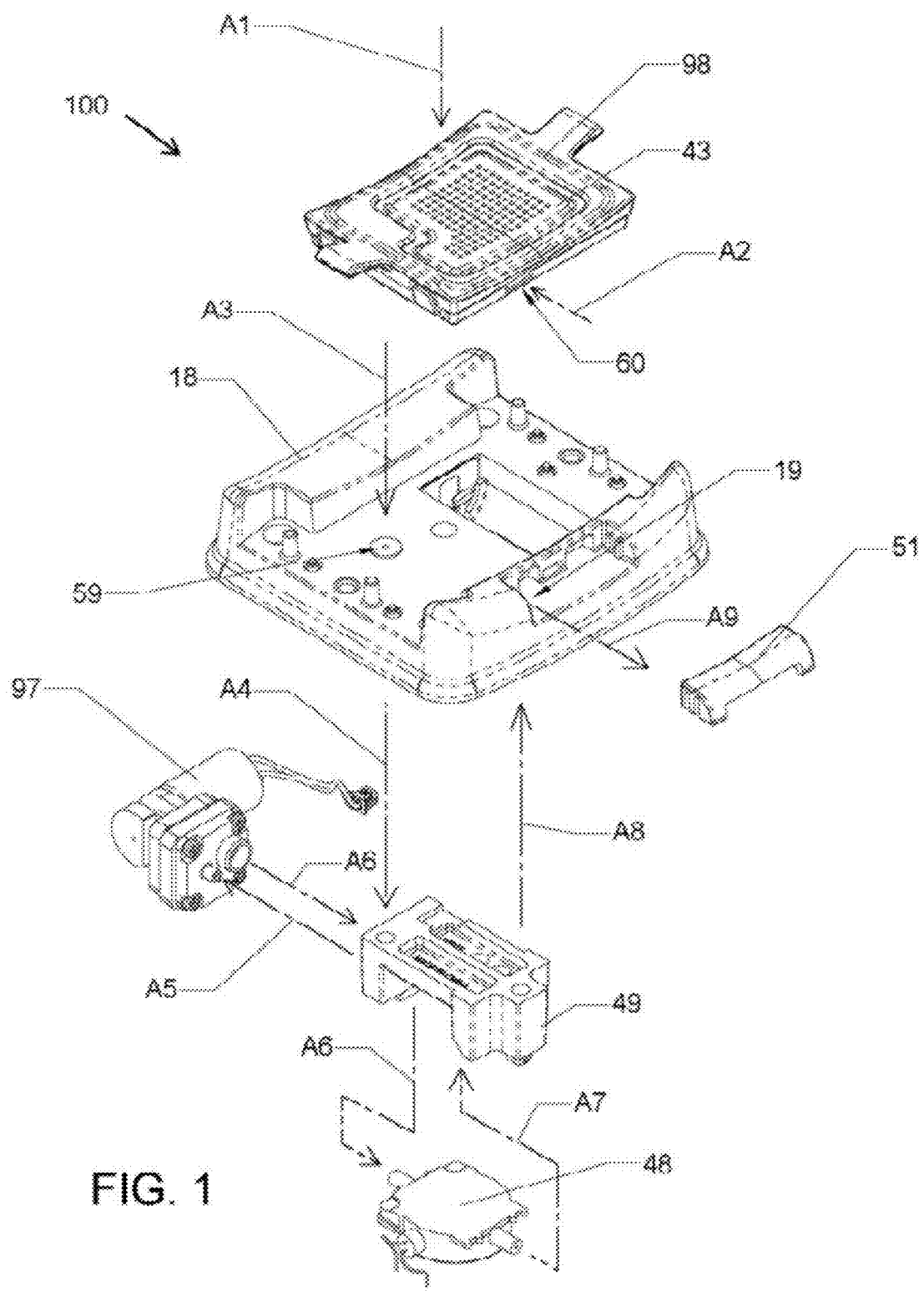
FIG. 1 shows an exploded perspective view of a transdermal alcohol monitor and the air flow path of an air sample through the various air flow path components, and the backflow of interferent into the fuel cell.

Referring now to the Figures, like reference numerals and names refer to structurally and/or functionally similar elements thereof, and if objects depicted in the figures that are covered by another object, as well as the tag line for the element number thereto, may be shown in dashed lines.

Figure 18:
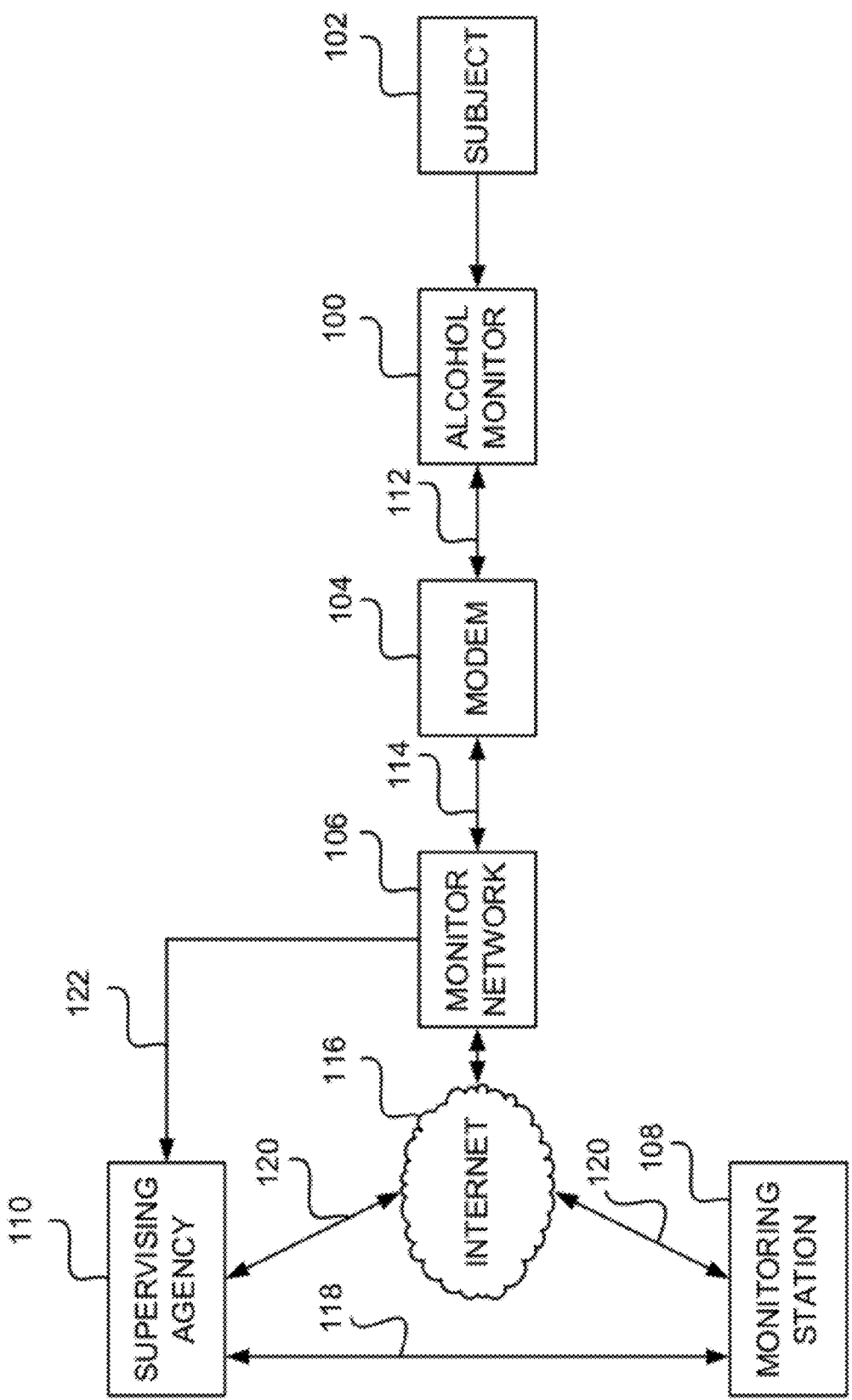
FIG. 18 shows a block diagram of an alcohol monitoring system of the present invention.

FIG. 18 shows a block diagram of an alcohol monitoring system of the present invention. Referring now to FIG. 18, in one embodiment, Transdermal Alcohol Monitor 100 is attached to the Subject 102. Many Transdermal Alcohol Monitors 100 may be attached to many Subjects 102 at the same time over a broad geographic area, and all may be monitored by Monitoring Station 108, which is the intended purpose. Likewise, there may be multiple Monitor Networks 106 and Monitoring Stations 108 that manage additional Subjects 102 in diverse geographic locations.

TAC readings are taken as scheduled without the participation of Subject 102, with the data uploaded at scheduled time intervals to Modem 104, or immediately if a positive drinking event or a tamper is detected and Modem 104 is in range. Typically, Modem 104 would be placed at the residence of Subject 102, and Subject 102 is merely required to periodically be in proximity to Modem 104 for the purpose of allowing automatic transmission of TAC measurements taken by Transdermal Alcohol Monitor 100 over a period of time. Subject 102 comes within range of Modem 104, typically within thirty feet, on a periodic basis, such as once per day, to allow the automatic transmission to take place. Different hardware components may increase or decrease the range at which the automatic transmission will take place. Subject 102 may rise and leave for work, return home, and remain at home until the next day when it is time to leave for work again. When Transdermal Alcohol Monitor 100 is in range and the timer indicates that it is time to communicate with Modem 104, Transdermal Alcohol Monitor 100 will transfer to Modem 104 through radio frequency ("RF") signals through bi-directional RF Communication Link 112 all the TAC readings, tamper indicators, error indicators, diagnostic data, and any other data stored in Transdermal Alcohol Monitor 100 regarding Subject 102. Modem 104 also can transmit operational information, such as monitoring schedules and reporting schedules in the form of RF signals back to Transdermal Alcohol Monitor 100 over bi-directional RF Communication Link 112.

Modem 104 stores the data contained in the RF signals received from Transdermal Alcohol Monitor 100 for transmission to Monitor Network 106. After receiving all of the information from Transdermal Alcohol Monitor 100, Modem 104 will check the stored data for any TAC readings, tampers, errors, or diagnostic data. Any one of these, or a trigger from a predetermined time interval, will cause Modem 104 to establish a connection over Communication Link 114 with Monitor Network 106. Once a connection is established, Monitor Network 106 validates the identity of Modem 104 and authenticates the data before it is stored. Once validated, Modem 104 will transfer all of the TAC readings, tampers, errors, diagnostic data, and any other data stored to a web-hosted database server at Monitor Network 106 where all data is permanently stored. Monitor Network 106 then analyzes the data received and separates and groups the data into a number of separate categories for reporting to monitoring personnel at Monitoring Station 108. The data can then be accessed by the monitoring personnel through the use of secured dedicated websites through the Internet 116 and Internet Connection 120 to Monitor Network 106. When Monitor Network 106 analyzes the data received, an automatic alert, based upon a rules-based database, may be sent directly from Monitor Network 106 to a call center at Supervising Agency 110 over Communication Link 122, or to an individual previously designated by Supervising Agency 110, when a specific alert, or combination of alerts, are received. The alert may be an e-mail, a fax, or a page to a previously provided number. Communication Link 122 may be a wire or wireless connection.

Monitor Network 106 may be located at Monitoring Station 108, or in a separate location. Monitoring personnel at Monitoring Station 108 have access to all of the data gathered on all of the Subjects 102. Supervising personnel at the call center of Supervising Agency 110, however, only have access to those Subjects 102 that are associated with Supervising Agency 110.

Monitoring Station 108 may automatically or periodically transmit data received from Modem 104 via Monitor Network 106 to one or more persons at Supervising Agency 110 who are assigned to monitor Subject 102, such as a parole officer, probation officer, case worker, or other designated person or persons in charge of enrolling Subject 102 and monitoring the data being collected on Subject 102. Only one Supervising Agency 110 is shown for simplicity, but one skilled in the art will recognize that many Supervising Agencies 110 may be accessing Monitor Network 106 at any given time. A connection is established with Supervising Agency 110 through Communication Link 118. Typically this connection is accomplished via the telephone system through a wire or wireless link, and may connect to a pager or cellular phone of the designated person. Designated personnel at Supervising Agency 110 may also access Monitor Network 106 through the use of secured dedicated websites through the Internet 116 and Internet Connection 120 to Monitor Network 106. Monitor Network 106 web software allows Supervising Agency 110 the ability to track Subject 102 compliance in a manner most feasible to them, and can be defined to fit the needs of both small and large programs. Each Supervising Agency 110 may customize the frequency of monitoring and the method of notification for alerts that they want to receive from Monitor Network 106. Alerts may be categorized by the type and severity of alert, allowing each Supervising Agency 110 to prioritize and better categorize a response (i.e., a low battery warning versus a possible alcohol violation).

Each Supervising Agency 110 has its own separate data storage area on the database server at Monitor Network 106 so that representatives from each Supervising Agency 110 can retrieve the secure data they need when they need it. Existing monitoring agencies that are experienced at managing alcohol offenders may easily take advantage of this approach.

Utilizing Transdermal Alcohol Monitor 100 with the system described has many advantages and benefits over existing methods and apparatus, including, but not limited to, no collection of body fluids (blood, breath, urine) that require special gathering, handling, or disposal considerations; no waiting for laboratory test results; there is no need for the subject to travel to a test center; continuous 24/7/365 monitoring and data collection from any location; no subject, agency official, or laboratory intervention—only passive participation on the part of the subject; the monitoring device is light weight and can be hidden from normal view; tamper-resistant technology ensures accurate readings representative of the subject being monitored; advanced technology utilizing microprocessors, encrypted data links, and secure data storage and retrieval; the ability for monitored subjects to maintain normal daily routines, including work, counseling, community service, family obligations, and recreation; and easy, web-based, secure access for the monitoring agency to each subject's data.

FIG. 1 shows an exploded perspective view of a Transdermal Alcohol Monitor 100 and the air flow path of a sample through the various air flow path components, and the back-flow of interferent into the fuel cell. Referring now to FIG. 1, an air flow path through Transdermal Alcohol Monitor 100 is described and indicated by arrows A1-A9. An air vapor sample (A1) is moved into Disposable Cartridge 98 from the skin of a subject through Inlet Plate 43 by Pump 97. Transdermal Alcohol Monitor 100 is worn by a subject, typically strapped around an ankle, with Disposable Cartridge 98 facing the skin of the subject. Ambient air is moved into (A2) Disposable Cartridge 98 through Cartridge Vent 60 in the side of Disposable Cartridge 98 by Pump 97. It should be noted that it is possible to operate the alcohol monitor without Pump 97 as long as the air flow path has no physical barriers. Since there is a fairly constant flow of insensible skin perspiration out from the skin of the subject, there is a positive force for moving the insensible skin perspiration through the air flow path once the alcohol monitor is attached to a limb of a subject. However, it has been found to be greatly advantageous to utilize Pump 97 to control the amount of air vapor sample that is passed through Fuel Cell 48, and for drawing in ambient air along with the air vapor sample from the skin of the subject into the sample collection chamber located below Inlet Plate 43 of Disposable Cartridge 98. Although this description focuses on the use of Fuel Cell 48, which utilizes a chemical process, and are available from many manufacturers, such as Dräger in one embodiment, other types of sensors may be utilized for detecting transdermal alcohol concentration, such as solid state sensors, such as the MiCS-5135 VOC Sensor from e2v Technologies (UK) limited. Various other models and brands of sensors may also be used. As such, and based upon which type of sensor is utilized, one skilled in the art will recognize that calculating an offset value may be based upon the current output from the alcohol sensor, or voltage from the current output from the alcohol sensor, or some other factor related to the alcohol sensor. In the embodiment described below, voltage from the current output from the alcohol sensor is the factor used. Such other embodiments are within the scope of this invention.

Pump 97 draws the combined air sample (air vapor sample and ambient air) (A3) from the sample collection chamber of Disposable Cartridge 98 through Cartridge Outlet 59 located in Inner Housing 18. The combined air sample is then moved (A4) into Fuel Cell Grommet 49 and into Pump 97 (A5), then moved back out of Pump 97 (A6) through Fuel Cell 48, where the combined air sample passes across the face of Fuel Cell 48 generating a TAC reading, and back into Fuel Cell Grommet 49 (A7). The combined air sample is moved (A8) back into Inner Housing 18 and then exits Inner Housing 18 through Exhaust Vent 19 located under Exhaust Cover 51 (A9) and to the ambient air outside of Inner Housing 18.

In order for the alcohol monitor to reliably measure transdermal alcohol content, the insensible skin perspiration which is emitted from the body in the form of air vapor will migrate away from the skin and through Inlet Plate 43 and into Disposable Cartridge 98 of Inner Housing 18. These air vapors collect in the sample collection chamber located in Disposable Cartridge 98 where it mixes with ambient air that is let in through Cartridge Vent 60. Pump 97 is activated to draw the combined air sample (air vapor and ambient air) from Disposable Cartridge 98, through Cartridge Outlet 59 into Fuel Cell Grommet 49, and into Pump 97. The air sample is then moved out of Pump 97 through Fuel Cell 48 into Fuel Cell Grommet 49, where it passes into Inner Housing 18 and out of Exhaust Vent 19.

In order to avoid false readings, it is important that the alcohol monitor be waterproof to prevent the entry of water directly into the air flow path. It is also important that any moisture in the air sample itself be removed, and any water condensation resulting from temperature changes between the point where the air sample enters into the alcohol monitor to the point where sensor measuring takes place is eliminated or minimized.

Moisture buildup inside an alcohol monitor is understandable, given that the source of the inlet air is directly from the subject's skin surface, which constantly emits water vapor in the form of insensible skin perspiration. The rate at which moisture builds up inside an alcohol monitor depends in part upon the subject, as each person has a varying amount of perspiration that their body gives off. Condensation of moisture into water droplets within a transdermal alcohol monitor can eventually damage internal components, thus reducing the service life of the transdermal alcohol monitor. When water buildup is too great within a transdermal alcohol monitor, the water may prevent alcohol readings from being taken. This is because alcohol is water soluble, and the fuel cell sensor will not sense the alcohol suspended in water. The alcohol monitor described in application Ser. No. 12/013,931 solves these water condensation problems associated with prior transdermal alcohol monitors. First, the air flow path was simplified by eliminating many of the physical barriers that trapped and retained moisture. Second, additional changes were made to the air flow path to take advantage of gravity, allowing any water droplets that form along the air flow path to flow out of the transdermal alcohol monitor while the subject is in an upright position (walking or standing). Third, by allowing ambient air to enter Disposable Cartridge 98, the humidity level was lowered from about 95% in the sample collection chamber to approximately 30%, which is fairly constantly maintained along the entire air flow path, thereby lowering the dew point temperature and causing the moisture in the sample to continue to be held in its vapor state. Thus, elimination of potential moisture condensation internal to the transdermal alcohol monitor was achieved.

However, the unrestricted air flow path above which helps eliminate the moisture build-up problem inside the transdermal alcohol monitor allows backflow of ambient air in a reverse direction along the airflow path from the arrows A9 to A8 to A7 to A6. Backflow will not proceed beyond A6 due to a check valve internal to Pump 97. When the ambient air contains an interferent, and the interferent-laden ambient air migrates into Fuel Cell 48. Naturally, Fuel Cell 48 reacts to the interferent. When a combined air vapor and ambient air sample is then pumped into the Fuel Cell 48, the TAC reading may result in a false positive, depending upon the amount of interferent in the ambient air, falsely indicating the consumption of alcohol (a drinking event) by the subject being monitored when in fact, there has been no drinking event at all. It is necessary to be able to detect the presence of interferents in order to eliminate the occurrence of such false positive readings.

Figure 2:
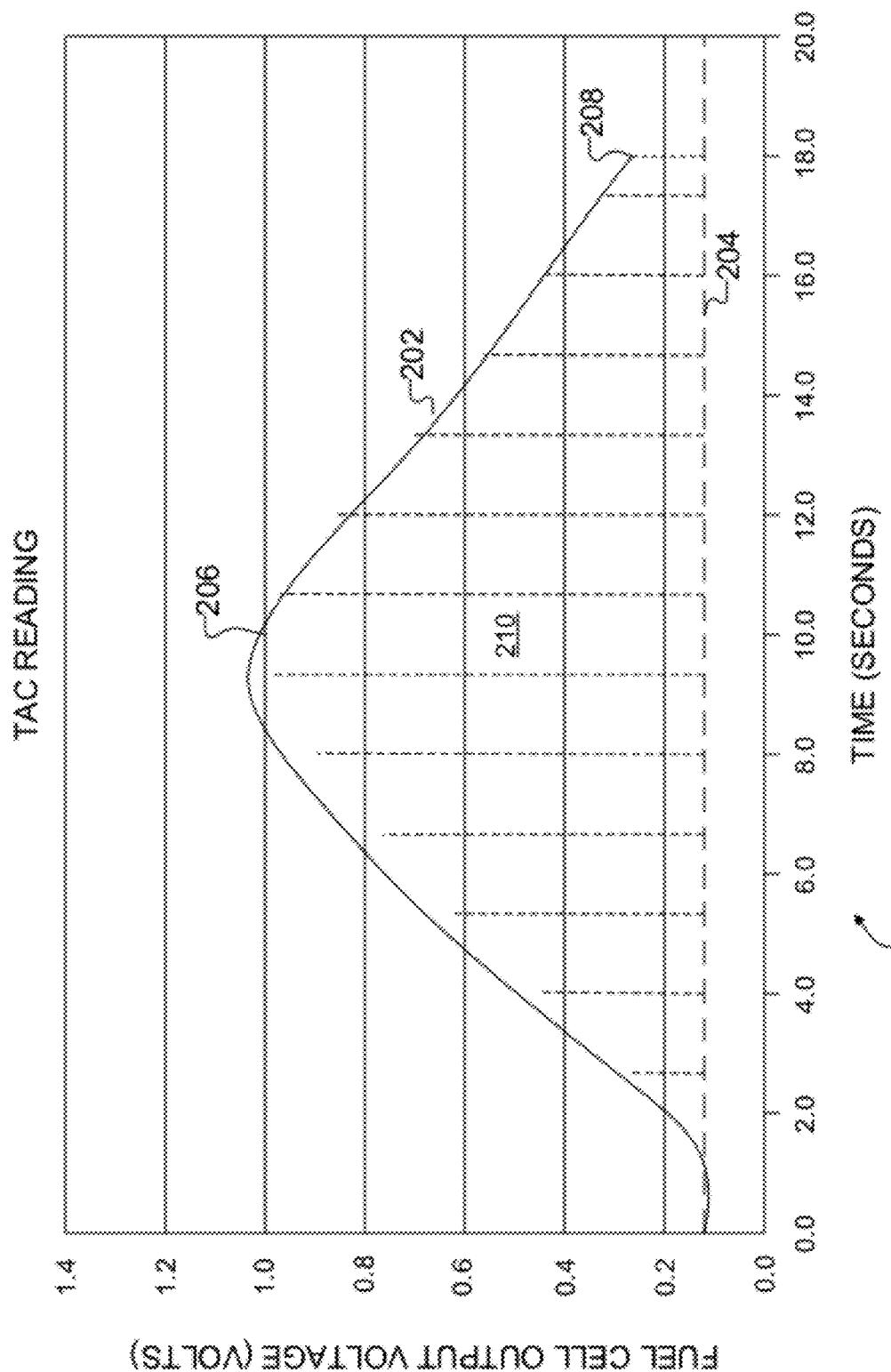
FIG. 2 shows a graph of a single TAC reading from a transdermal alcohol monitor.

FIG. 2 shows a graph of a single TAC reading from a transdermal alcohol monitor. Referring now to FIG. 2, Graph 200 shows the relationship between fuel cell output voltage versus time for a TAC reading for Transdermal Alcohol Monitor 100 shown in FIG. 1. This relationship is plotted as TAC Curve 202. First, Transdermal Alcohol Monitor 100 takes a voltage reading of Fuel Cell 48 in order to obtain a baseline voltage prior to introducing the sample which has been collected in the sample collection chamber. This baseline voltage reading becomes Baseline Voltage 204 for the TAC reading. Transdermal Alcohol Monitor 100 then activates Pump 97 and draws the sample vapor out of the sample collection chamber and introduces it into Fuel Cell 48. The output voltage from Fuel Cell 48 is tracked while it reaches a Peak Value 206, and then declines until it reaches a level equal to 20% of Peak Value 206 minus Baseline Voltage 204, shown as 20% Level 208. Once 20% Level 208 is reached, the Area 210 (shown in hashed line) beneath the curve up to 20% Level 208 point is calculated by an evaluation circuit in Transdermal Alcohol Monitor 100 to determine the transdermal alcohol level of the sample, and is expressed as a percent of weight of alcohol to volume (% w/v). The area shown in hashed lines enclosed between the function value of the measurement signal and Baseline Voltage 204 is proportional to the concentration of the alcohol vapor in the sample. The larger the area under the curve, the higher the concentration of alcohol vapor in the sample.

Figure 3:
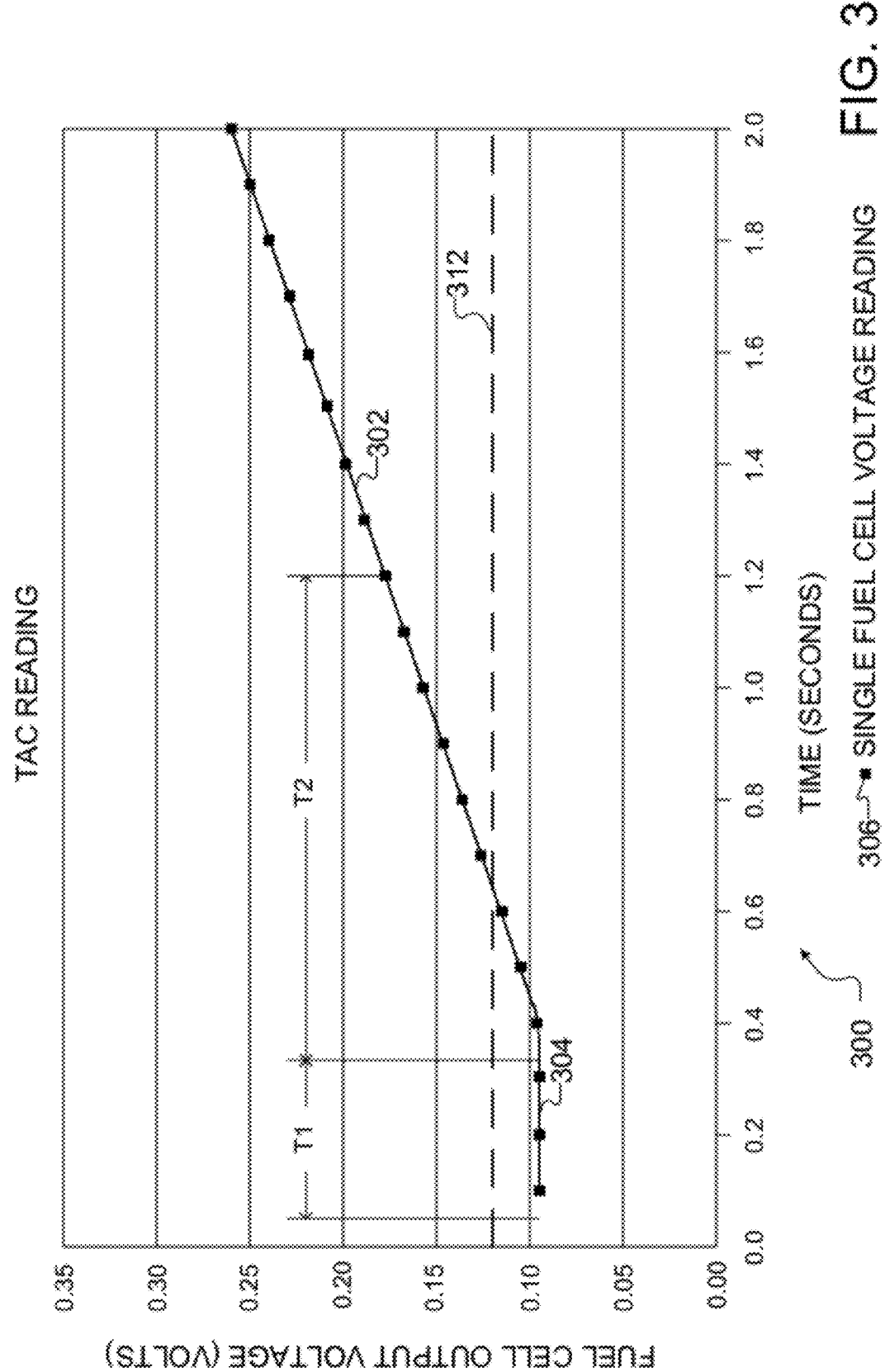
FIG. 3 shows a graph of the first two seconds of a TAC reading in the absence of any environmental interferents.

FIG. 3 shows a graph of the first two seconds of a TAC reading, such as shown in FIG. 2, in the absence of any environmental interferents. Referring now to FIG. 3, Graph 300 shows that at the beginning of a TAC reading, Transdermal Alcohol Monitor 100 during time span T1 takes three Fuel Cell Voltage Readings 306 within the first zero to approximately 0.4 seconds and averages these three readings to obtain the Baseline Voltage 304 for this TAC reading. More or fewer readings than three may be used, but three has been shown to be sufficient and useful. Next, during time span T2, Pump 97 is run for approximately 0.8 seconds, drawing the sample from the sample collection chamber into Fuel Cell 48. Fuel Cell Voltage Readings 306 from Fuel Cell 48 are used to obtain TAC Curve 302 during time span T2 and beyond. One skilled in the art will recognize that T1 and T2 may be adjusted individually or in combination to longer or shorter periods of time based upon the desired goals or outcomes or as a result of empirical testing and results. The timeframes listed above have been shown to be useful and sufficient for a particular embodiment and application. Over time, multiple Baseline Voltage 304 readings are gathered and stored for TAC readings that measured less than about 0.001% w/v transdermal alcohol concentration or there about. The average of these multiple Baseline Voltage 304 readings is calculated. Maximum Fuel Cell Voltage Line 312 represents a maximum voltage that is about ten percent over the calculated average baseline voltage. For the TAC reading shown in Graph 300, Baseline Voltage 304 is below Maximum Fuel Cell Voltage Line 312, indicating that there are no interferents present in this TAC reading. One skilled in the art will recognize that the 0.001% and ten percent values may be adjusted individually or in combination to higher or lower values based upon the desired goals or outcomes (e.g., more or less sensitivity) or as a result of empirical testing and results. The values listed above have been shown to be useful and sufficient for a particular embodiment and application, and other minimum ranges about plus-or-minus 0.001% w/v and maximum ranges about plus-or-minus ten percent are within the scope of the invention.

Figure 4:
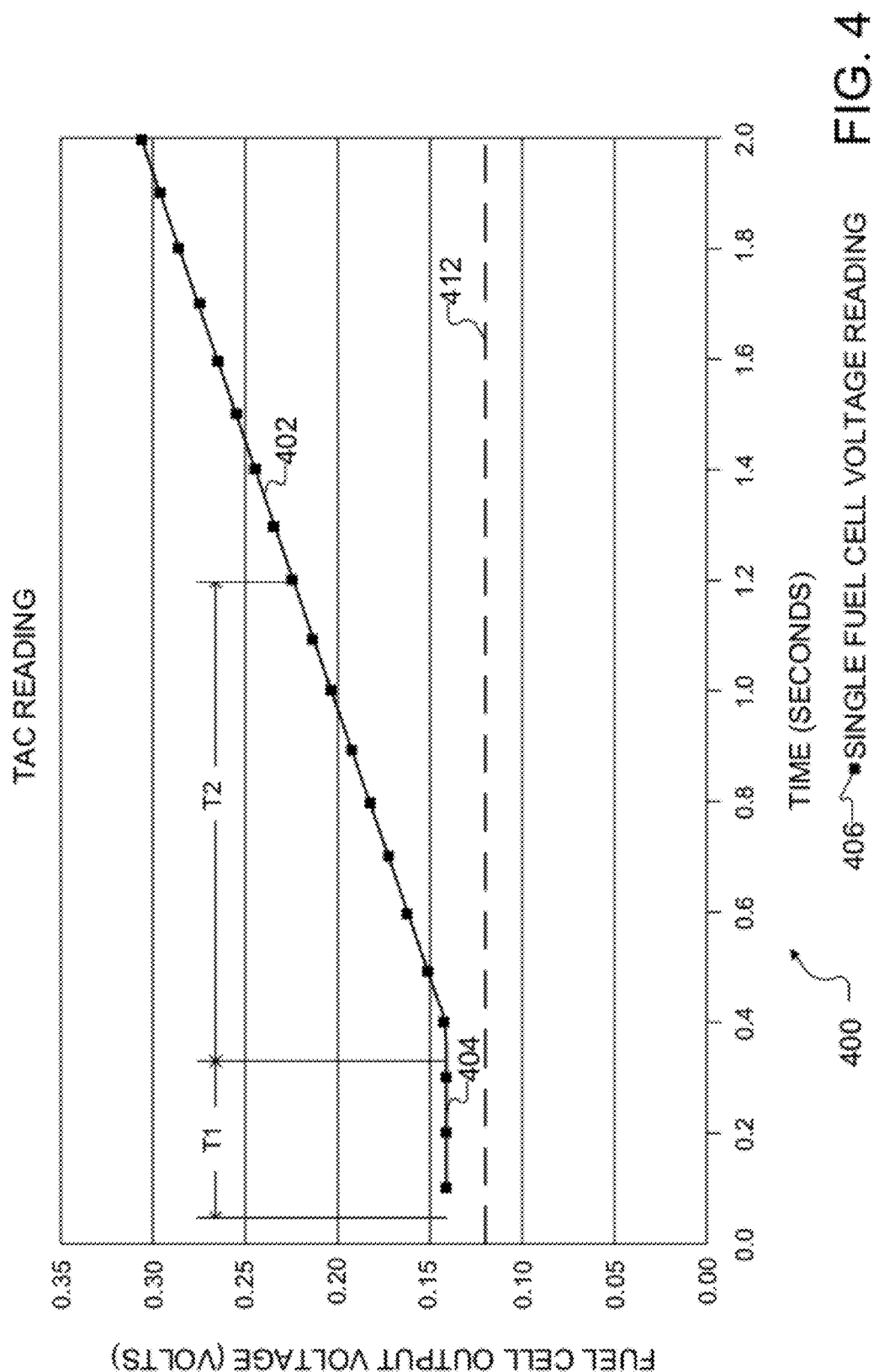
FIG. 4 shows a graph of the first two seconds of a TAC reading in the presence of environmental interferents.

FIG. 4 shows a graph of the first two seconds of a TAC reading in the presence of environmental interferents. Referring now to FIG. 4, when environmental interferents are introduced into the location where a subject is wearing Transdermal Alcohol Monitor 100, the interferents may, over time, backflow along the airflow path from the arrows A9 to A8 to A7 to A6 as described above in FIG. 1 and arrive at Fuel Cell 48. Fuel Cell 48 will naturally react to the small trace levels of interferent by producing small levels of voltage. Thus, when the next TAC reading is taken, the first three Fuel Cell Voltage Readings 406 will show an increase in the voltage level. When this increased level of voltage measures over ten percent of the calculated baseline voltage average, then the TAC reading is deemed to have occurred in the presence of an environmental interferent. This TAC reading may be disregarded in order to avoid a false positive reading when evaluated in the context of the TAC readings taken before and after this TAC reading.

Environmental interferents may be found in bars, bakeries, barber shops, hair salons, and other locations where menthol, propanol, isopropanol, ethanol, and other similar compounds are present. These gaseous compounds can cause Fuel Cell 48 to react if they backflow into Transdermal Alcohol Monitor 100. For example, as bread dough rises, yeast in the rising process gives off ethanol into the air. If a subject wearing Transdermal Alcohol Monitor 100 happens to be in a poorly ventilated bakery where ethanol in the air is present for a sufficient amount of time, some of the ethanol in the air may backflow into Fuel Cell 48 and cause elevated fuel cell voltage readings.

Graph 400 shows that at the beginning of a TAC reading, Transdermal Alcohol Monitor 100 during time span T1 takes three fuel cell voltage readings within the first zero to approximately 0.4 seconds and averages these three readings to obtain the Baseline Voltage 404 for this TAC reading. Next, during time span T2, Pump 97 is run for approximately 0.8 seconds, drawing the sample from the sample collection chamber into Fuel Cell 48. Readings from Fuel Cell 48 are used to obtain TAC Curve 402 during time span T2 and beyond. Maximum Fuel Cell Voltage Line 412 represents a voltage that is ten percent over the average baseline voltage calculated from previous TAC readings as described above for Transdermal Alcohol Monitor 100. For the TAC reading shown in Graph 400, Baseline Voltage 404 is above Maximum Fuel Cell Voltage Line 412, indicating that this TAC reading has been taken in the presence of an interferent.

Figure 5:
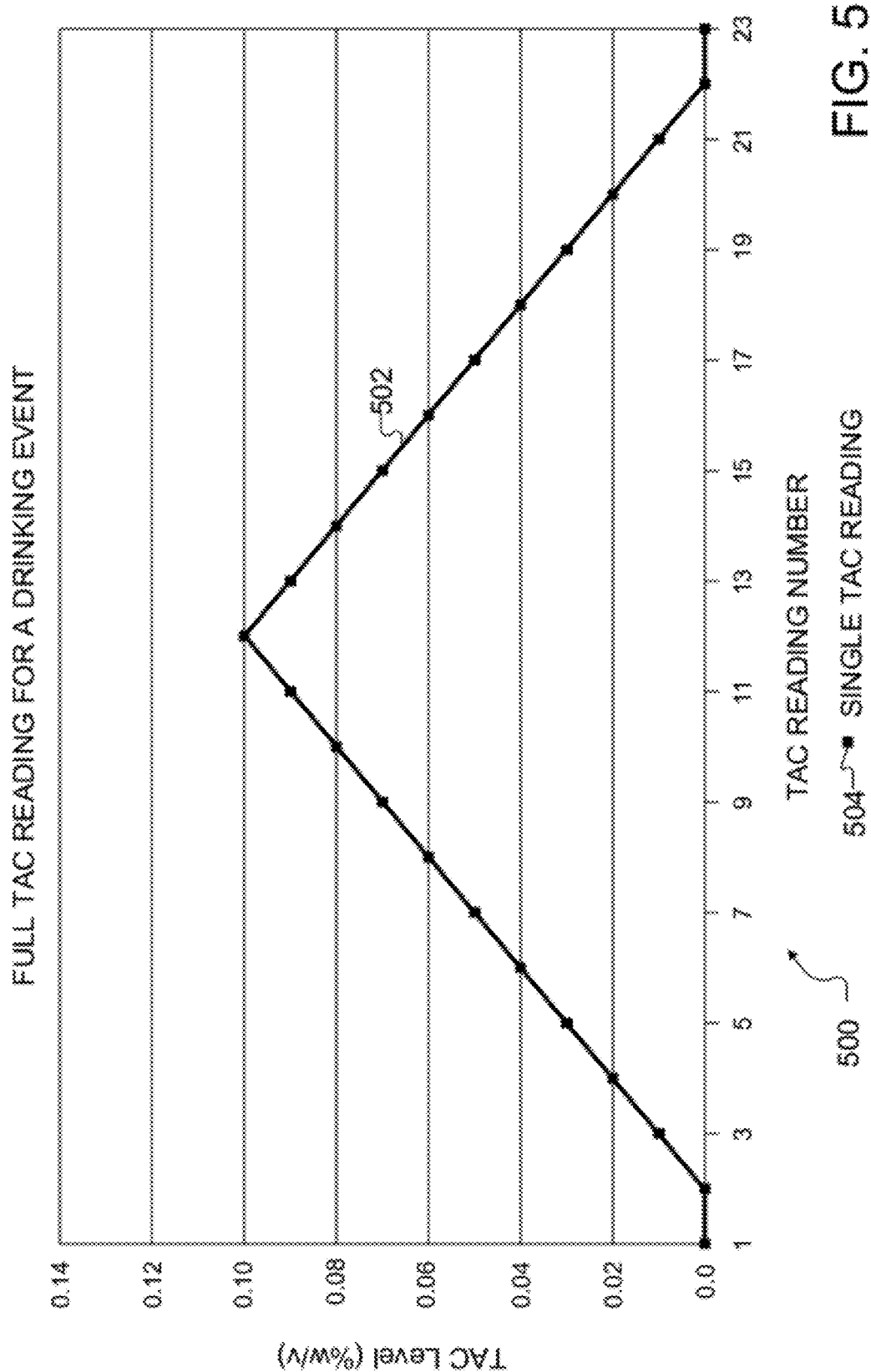
FIG. 5 shows an entire drinking event monitored transdermally by a transdermal alcohol monitor.
Figure 6:
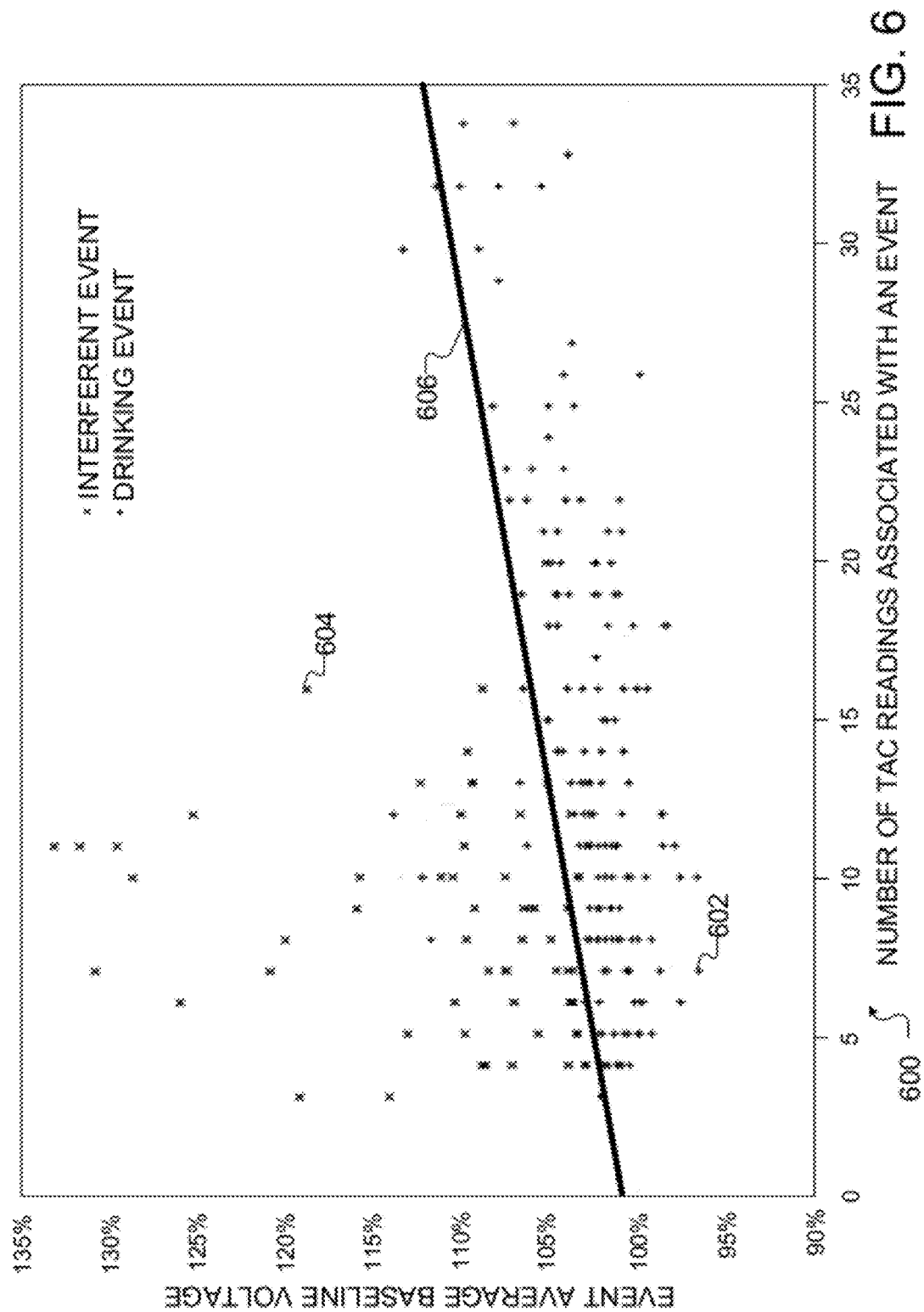
FIG. 6 shows the results of empirical testing to determine the relationship between the average baseline voltage for drinking events and interferent events.

In another embodiment of the invention an average of the baseline voltages for a series of individual TAC readings that are less than 0.001% w/v transdermal alcohol concentration can also be used to identify the presence of an environmental interferent in a monitored event. Referring now to FIG. 5, Graph 500 shows an entire drinking event monitored transdermally by Transdermal Alcohol Monitor 100. The Drinking Event Curve 502 is made up of multiple single TAC Readings 504, such as TAC Reading 200 shown in FIG. 2, over a series of 23 individual readings. The Y axis indicates the TAC readings, expressed in a percent of weight to volume, which is derived from the area under the curve (Area 210 in FIG. 2) for each individual TAC reading. The X axis indicates the individual number of TAC readings taken approximately once every thirty minutes. To use this method the baseline voltage for each individual TAC reading below 0.001% w/v will be averaged from the time the bracelet was attached to the subject to the time that the suspected drinking event in question occurs. This average value will be known as the average baseline voltage for the transdermal alcohol monitor worn by this subject. Then the average baseline voltage for each individual TAC reading in the suspected drinking event in question that is greater than or equal to 0.02% w/v will be calculated. This average value is referred to as the event average baseline voltage for the suspected drinking event in question. The 0.02% w/v value is the minimum value required to send an alert to a monitoring station that a drinking event has been detected. The maximum allowable average baseline voltage limit for the subject must then be calculated. FIG. 6 describes the basis for this calculation. One skilled in the art will recognize that the 0.02% value may be adjusted to a higher or lower value based upon the desired goals or outcomes or as a result of empirical testing and results. The value listed above has been shown to be useful and sufficient for a particular embodiment and application.

FIG. 6 shows the results of empirical testing to determine the relationship between the average baseline voltage for drinking events and interferent events. Graph 600 shows the plotting of data points where the X axis represents the total number of TAC readings associated with either a drinking event or an interferent event that are above 0.02% w/v, and the Y axis represents the event average baseline voltage for the drinking event or the interferent event. For the drinking events, a test subject wearing a Transdermal Alcohol Monitor 100 consumed alcohol in varying amounts over varying lengths of time. Drinking events are plotted on Graph 600 as a "+" character. For the interferent events, a test subject wearing a Transdermal Alcohol Monitor 100 did not drink but was placed in an environment having gaseous interferents of various kinds over various periods of time. Interferent events are plotted on Graph 600 as an "×" character. For example, Drinking Event 602 represents seven individual TAC readings with an average baseline voltage for the drinking event of 96% (TAC readings above 0.02% w/v). This means that the event average baseline voltage for the set of seven readings in the drinking event is 96% of the calculated average baseline voltage for the particular Transdermal Alcohol Monitor 100 worn by the subject since the subject put on the particular Transdermal Alcohol Monitor 100. Event average baseline voltage readings less than 100% are due to the natural drift in the sensor over time. Interferent Event 604 represents sixteen individual TAC readings with an event average baseline voltage for the interferent event of 119%.

By observing the data plotted in Graph 600, it is apparent that interferent events plot predominately on the top portion of Graph 600, and drinking events plot predominately on the bottom portion of Graph 600. By applying a best curve fitting technique to the data points, a Best Fit Curve 606 can be drawn. Best Fit Curve 606 intersects the Y axis at approximately 101% Event Average Baseline Voltage for the events and has a slope of 0.0033. In the example shown in FIG. 6, a straight line is used. One skilled in the art will recognize that in addition to a straight line, a combination of two or more connecting straight lines, a curve, or a step function could also be used to obtain a best fit curve. These different embodiments are within the scope of the invention.

The maximum allowable average baseline voltage limit for a subject is calculated based upon Best Fit Curve 606. The base value of 101% will be added to the number of TAC readings in the event that are greater than or equal to 0.02% w/v multiplied by 0.0033. This will produce the maximum allowable average baseline voltage limit that the suspected drinking event must not be greater than. If the average baseline voltage for the suspected drinking event is greater than the calculated maximum allowable average baseline voltage limit, then the event is deemed to contain some sort of environmental interferent. The TAC reading is therefore disregarded as a non-drinking event, and no alert is sent to the monitoring station or supervising agency.

Figure 7:
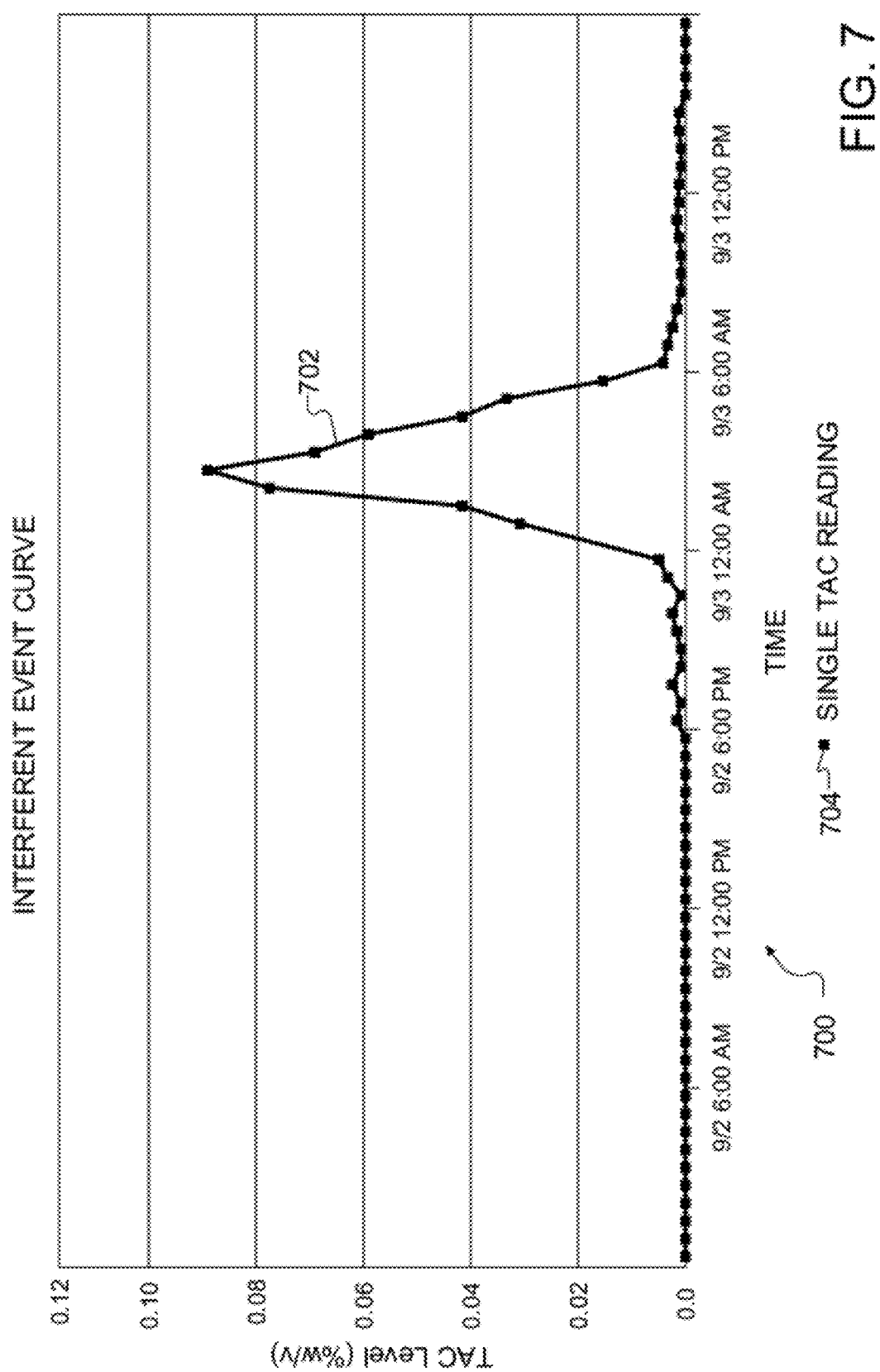
FIG. 7 shows an example of an actual interferent curve recorded for a test subject wearing a transdermal alcohol monitor in an environment having one or more interferents.

FIG. 7 shows an example of an actual interferent curve recorded for a test subject wearing a transdermal alcohol monitor in an environment having one or more interferents, such as a bar or a bakery. Graph 700 shows that a multiple number of TAC readings for this event were received from Transdermal Alcohol Monitor 100. The Y axis indicates the individual TAC readings, expressed in a percent of weight to volume. The X axis indicates the individual number of TAC Readings 704 for an event taken over approximately a twenty-four hour period. The Interferent Event Curve 702 is plotted from the individual TAC readings. Eight of the TAC readings recorded had a value greater than or equal to 0.02% w/v, which could be an indication of a drinking event. The average baseline voltage for this subject at the time the event began was 0.134 volts, and the maximum allowable average baseline voltage for this event is calculated as follows: (1.01+(0.0033*8))*100=103.64% over the average baseline voltage, which is equal to 0.138 volts (0.134 volts*103.64%). The event average baseline voltage for the TAC readings over 0.02% w/v was recorded to be 0.143 volts, or 106.7% over the average baseline voltage (0.143 volts divided by 0.134 volts). Therefore, this event would be correctly identified as an interferent event and not a drinking event since the event average baseline voltage for the TAC readings over 0.02% w/v (0.143 volts) exceeds the calculated maximum allowable average baseline voltage (0.138 volts). And in fact, the test subject did visit a bar for a period of time, but did not consume any alcohol. The bar environment contains gaseous interferents that were detected by Transdermal Alcohol Monitor 100.

Figure 8:
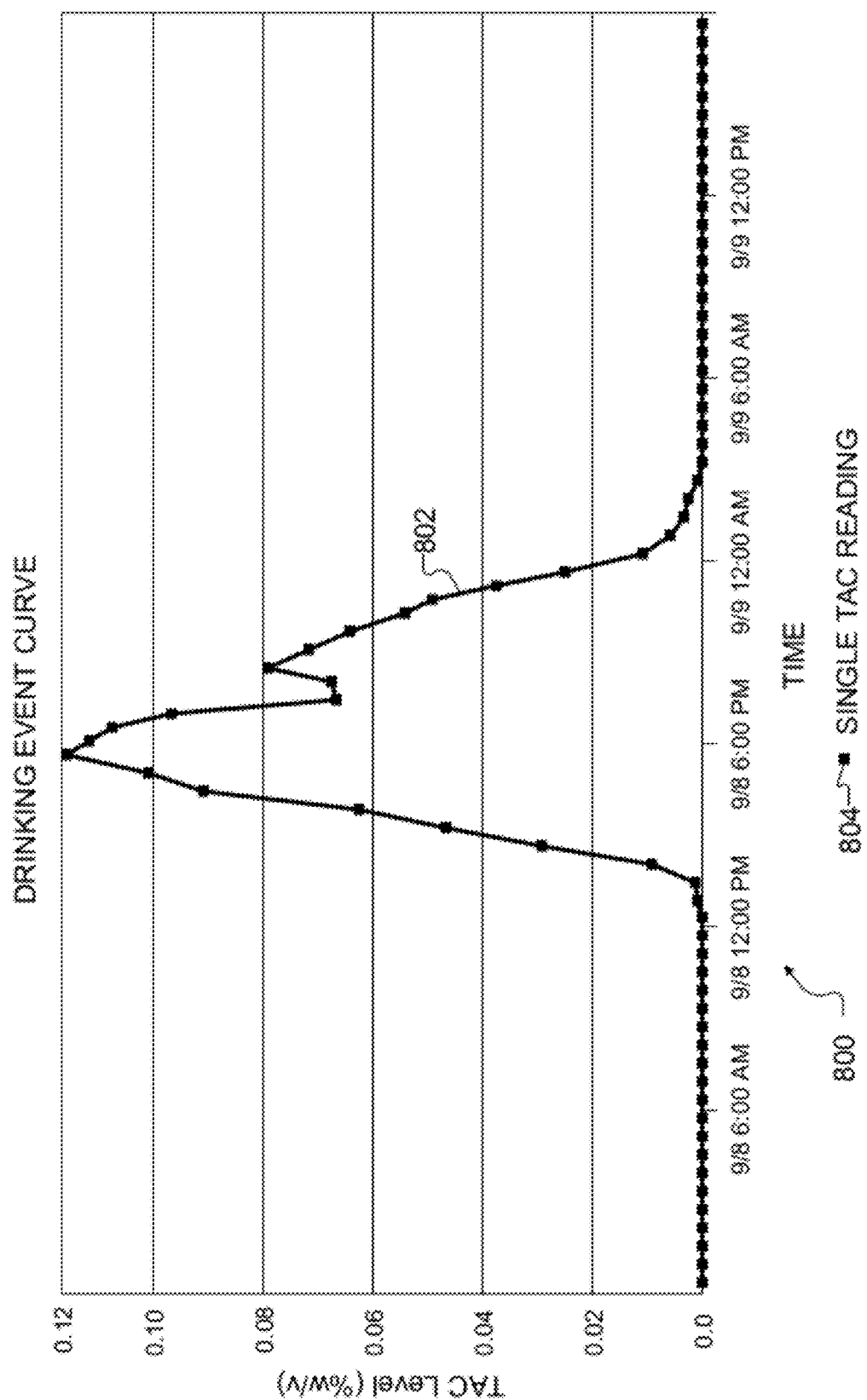
FIG. 8 shows an example of an actual drinking curve recorded for a test subject wearing a transdermal alcohol monitor who has consumed alcohol.

FIG. 8 shows an example of an actual drinking curve recorded for a test subject wearing a transdermal blood alcohol monitor who has consumed alcohol. Graph 800 shows that a multiple number of TAC readings for this event were received from Transdermal Alcohol Monitor 100. The Y axis indicates the TAC readings, expressed in a percent of weight to volume. The X axis indicates the individual number of TAC Readings 804 taken over approximately a twenty-four hour period. The Drinking Event Curve 802 is plotted from the individual TAC readings. Eighteen of the TAC readings recorded had a value greater than or equal to 0.02% w/v, which could be an indication of a drinking event. The average baseline voltage for this subject at the time the event began was 0.134 volts, and the maximum allowable average baseline voltage for this event is calculated as follows: (1.01+(0.0033*18))*100=106.94% over the average baseline voltage, which is equal to 0.143 volts (0.134 volts*106.94%). The event average baseline voltage for the TAC readings over 0.02% w/v was recorded to be 0.136 volts or 101.5% over the average baseline voltage (0.136 volts divided by 0.134 volts). Therefore, this event would be correctly identified as a drinking event since the event average baseline voltage for the TAC readings over 0.02% w/v (0.136 volts) is less than the calculated maximum allowable average baseline voltage (0.143 volts). And in fact, the test subject did consume a quantity of alcohol.

Thus, even though the interferent event shown in FIG. 7 and the drinking event shown in FIG. 8 have a similar shaped event curves 702 and 802, applying the above methodology to the TAC readings and voltage readings gathered by Transdermal Alcohol Monitor 100 during the monitored event, a determination can be made as to what is a true drinking event and an event that is the result of an interferent.

Figure 9:
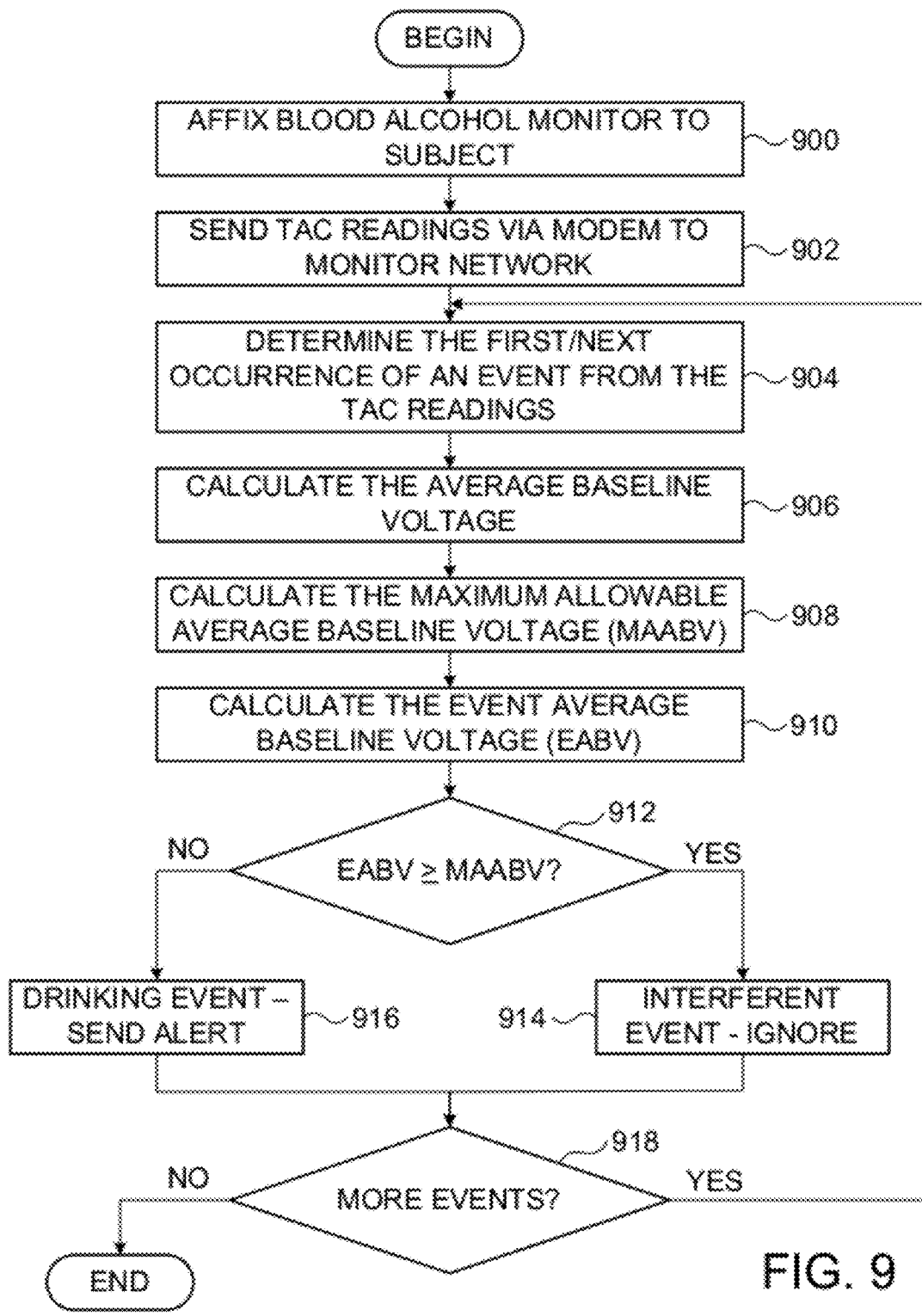
FIG. 9 shows a flow chart of a general method of an embodiment of detecting an environmental interferent in a transdermal alcohol monitor.

FIG. 9 shows a flow chart of a general method of an embodiment of detecting an environmental interferent in a transdermal alcohol monitor. Referring now to FIG. 9, the method begins in step 900 by affixing Transdermal Alcohol Monitor 100 to a subject. Transdermal Alcohol Monitor 100 begins taking TAC readings, typically according to a predetermined schedule, which may be altered or updated from time-to-time. The TAC readings are stored in Transdermal Alcohol Monitor 100 and are transmitted in step 902 to a modem that is located typically in the home of the subject being monitored. The modem transmits the TAC readings to a monitor network on a predetermined basis, or upon establishing a link to Transdermal Alcohol Monitor 100 when the subject returns to his home after being away for a period of time. The monitor network has one or more computing devices for processing the TAC readings received from multiple subjects. In step 904 the monitor network evaluates the TAC readings received to determine the occurrence of an event, which may be a drinking event or an interferent event. Upon detecting an event, in step 906 the computing device in the monitor network calculates an average baseline voltage for the Transdermal Alcohol Monitor 100 worn by the subject, as described above, since the time that the subject began wearing Transdermal Alcohol Monitor 100. In step 908 the computing device in the monitor network calculates a maximum allowable average baseline voltage (MAABV) for Transdermal Alcohol Monitor 100 based upon the average baseline voltage as described above. The computing device in the monitor network in step 910 calculates an event average baseline voltage (EABV) for (TAC) readings in the event that have a value greater than or equal to 0.02% w/v as described above. In comparison step 912 the computing device in the monitor network compares the EABV to the MAABV. If the EABV is greater than or equal to the MAABV, then control flows to step 914 which categorizes the event as an interferent event, and the event is ignored. If the EABV is less than the MAABV, then control flows to step 916 which categorizes the event as a drinking event, and an alert is sent from the computing device in the monitor network to one or more interested parties, such as a monitoring station or a supervising agency, as described in related U.S. Pat. No. 7,462,149. Control flows from both steps 914 and 916 to decision step 918 to determine if there are more events to be evaluated. If yes, control returns to step 904. If no, then the method ends.

Figure 17:
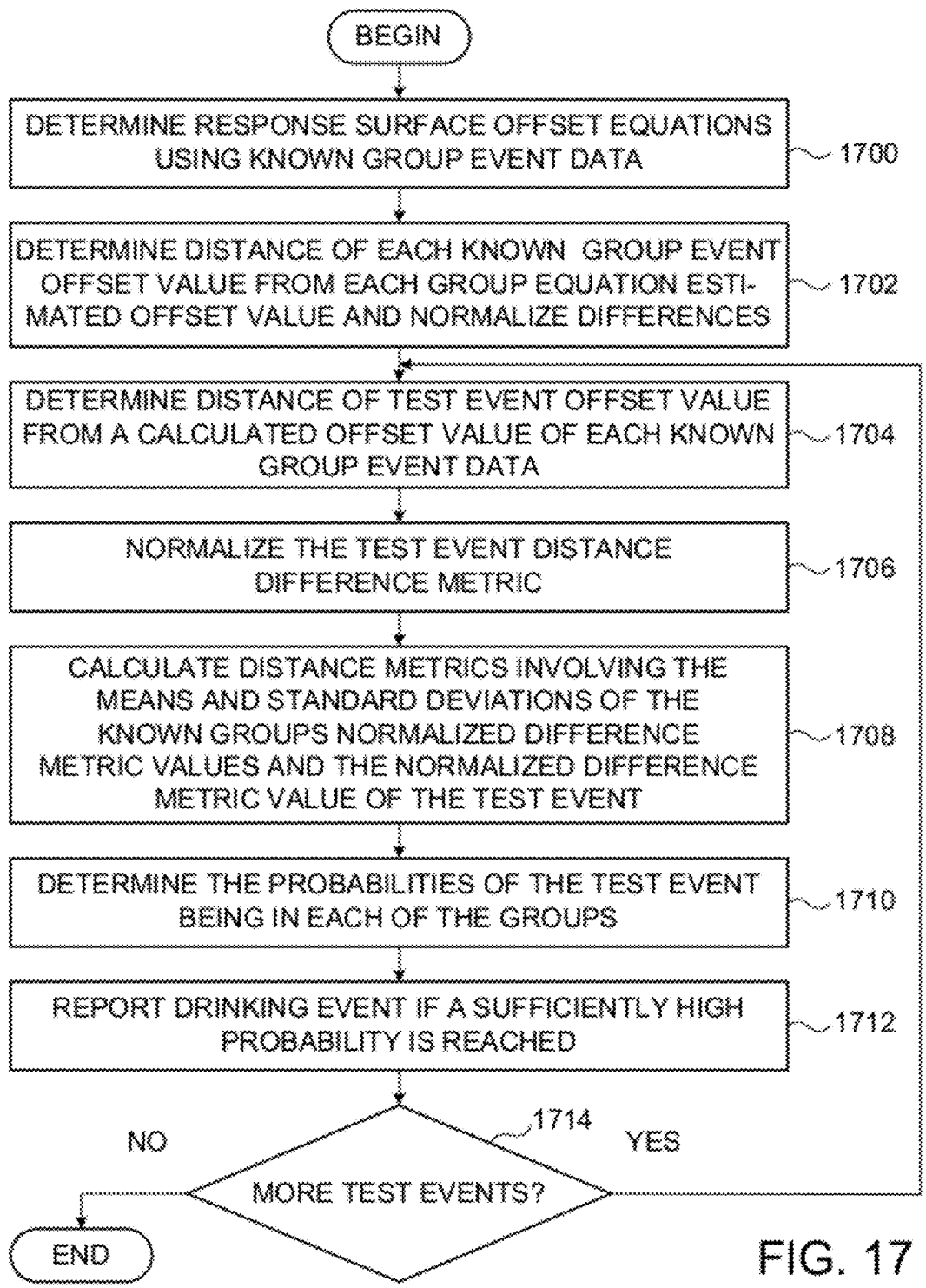
FIG. 17 shows a method for determining a drinking event from an interferent event through utilizing a normalized distance metric.

FIG. 17 shows a further refinement to determining a drinking event from an interferent event. This approach utilizes a normalized distance metric method for distinguishing drinking events from interferent events. This method measures an event type in terms of the relative closeness of an observed offset value of a test event to known interferent and drinking event populations of offset values. As shown in FIG. 18, Transdermal Alcohol Monitor 100 is designed to be used within a system that includes Modem 104 that communicates with Transdermal Alcohol Monitor 100. Modem 104 in turn communicates with Monitor Network 106 which maintains servers and databases to store and analyze the data collected from one or more Transdermal Alcohol Monitor s 100. The steps outlined in FIG. 17 are typically achieved by a processor located within Monitor Network 106, but could also be performed in a different location.

Referring now to FIG. 17, the method begins in step 1700 where metrics are determined from Transdermal Alcohol Monitor 100 about known event type groups: drinking events and interferent events. Specifically, a response surface equation is determined for each of the known event type groups using the offset value as a function of the event number of TAC readings, the absorption and elimination rates of the subject's skin, and the peak TAC reading. In step 1702 the distance of each group known event offset value from each group estimated value is determined as the absolute value of the difference between the observed and equation computed offset values. The group involving the smallest distance will tend to be the one in which the event should be classified. The subsequent absolute value distance difference metric values for the events relative to the known interferent and drinking event populations are usually not normally distributed. This is a requirement for subsequent metrics in this method. Thus, the distance differences are normalized.

The strategy of testing an unknown test event relative to the known populations begins in step 1704. The distance of the test event offset value from the estimated offset value from each known group equation calculated offset value is determined for each group. In step 1706 the distance difference metrics for the test event is normalized. The subsequent distance metrics used in calculating the classification probabilities assume that the metric values follow a normal distribution. The probabilities that the event falls in each of the two groups are then determined by the relative closeness of the normalized distance difference metric value for the test event to the mean metric normalized values of the known interferent and known drinking groups. The probability of an event being from one of the two populations can then be estimated using two final normalized distance metrics in step 1708 involving the means and standard deviations of the known population normalized difference metric values and the normalized difference metric value of the test event. The resulting probabilities are used in step 1710 to enable a better estimate of the likelihood that an event resulted from an ambient interferent or from drinking alcohol. Reporting decisions in step 1712 can be made based upon the level of probability that is desired on a predetermined basis, where the probability desired is chosen sufficiently high enough to satisfy specified criteria, such as legal standards, or reporting agency preferences. Test events falling below the level of probability desired are not reported, whereas test events above the level of probability desired are reported as drinking events. Step 1714 determines if there are more test events to be evaluated. If yes, control returns to step 1704. If not, then the method ends.

Interferent and Drinking Event Groups

Figure 10:
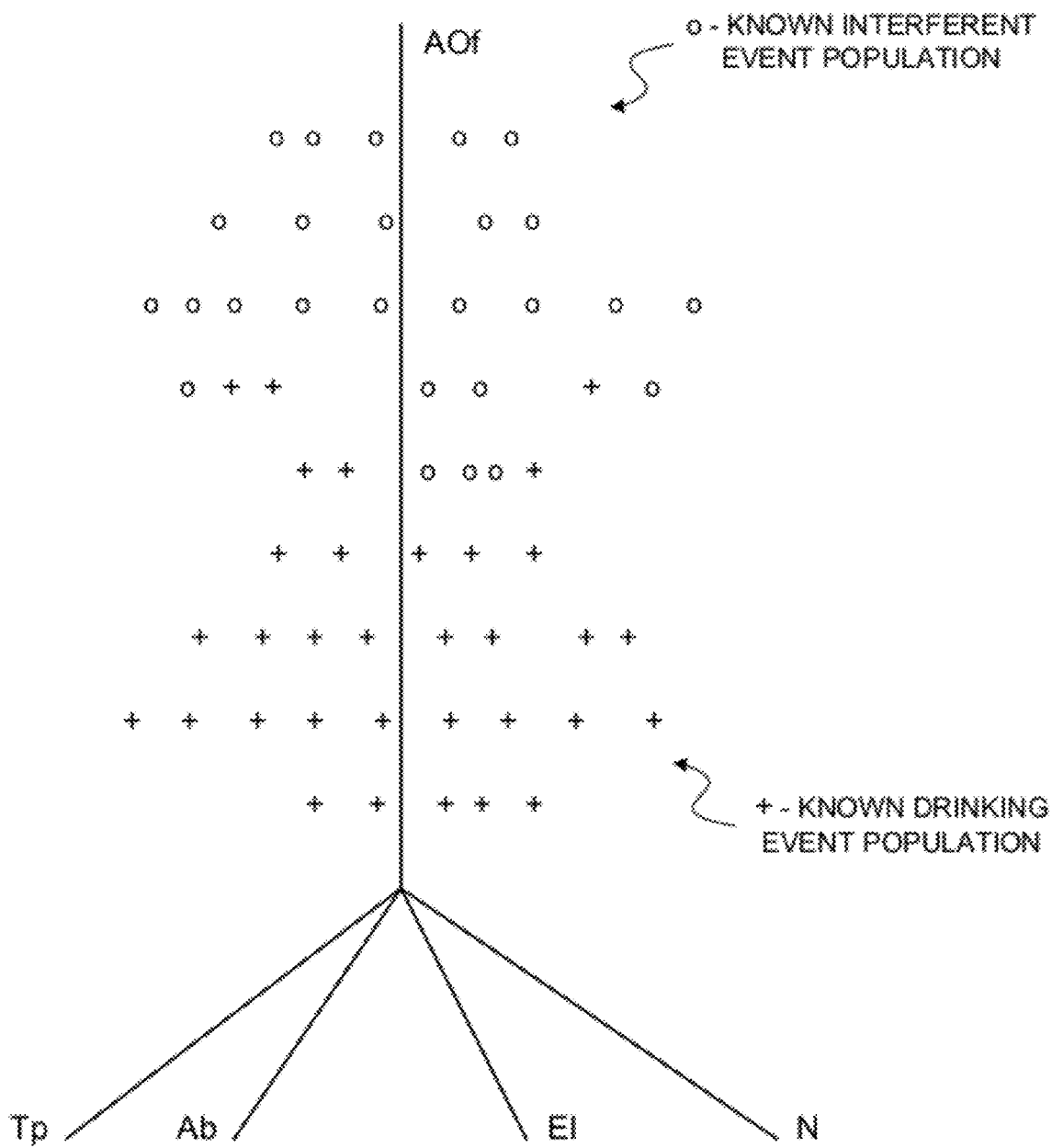
FIG. 10 shows a five-dimensional representation of known interferent and drinking event data.

FIGS. 10-16 further explain the method described in FIG. 17. The offset values for each Individual Transdermal Alcohol Monitor 100 are due to the effects of certain event parameters. These event parameters include the number of TAC readings, the absorption rate of alcohol of the subject, the elimination rate of alcohol of the subject, and the peak TAC reading for an event. These variables have a highly interactive and nonlinear effect on the offset value for each Individual Transdermal Alcohol Monitor 100. By constructing a data base of known interferent and drinking events, the data representing these event types can be split into two groups. A visual example of this is shown in FIG. 10 which is a five-dimensional representation of the data. The known interferent and drinking event populations are shown with an "o" character representing interferent events and a "+" character representing drinking events, respectively. Each point corresponds to specific values of the Transdermal Alcohol Monitor 100 average percent offset value/100 (AOf) for an event, the peak TAC reading for the event (Tp), the absorption rate of alcohol for the subject (Ab), the elimination rate of alcohol for the subject (El), and the total number of TAC readings (N) for a population. As shown in FIG. 10, some of the population points may overlap so that the populations are not totally disjoint. Interferent average percent offset values/100 (AOf) tend to be larger than for drinking average percent offset values, but not always.

The example shown in FIG. 10 is a function in the form of AOf=(Tp, Ab, El, N). One skilled in the art will recognize that the function could be expressed in terms of any of the factors listed, such as Ab=(Tp, AOf, El, N). In addition, the function could be expressed in terms of additional variables not shown, or fewer variables than those shown, and various combinations of the different variables. The variables and functions described above have proven to be useful and sufficient for a particular embodiment and application.

Surface Fits to Interferent and Drinking Event Groups

Figure 11:
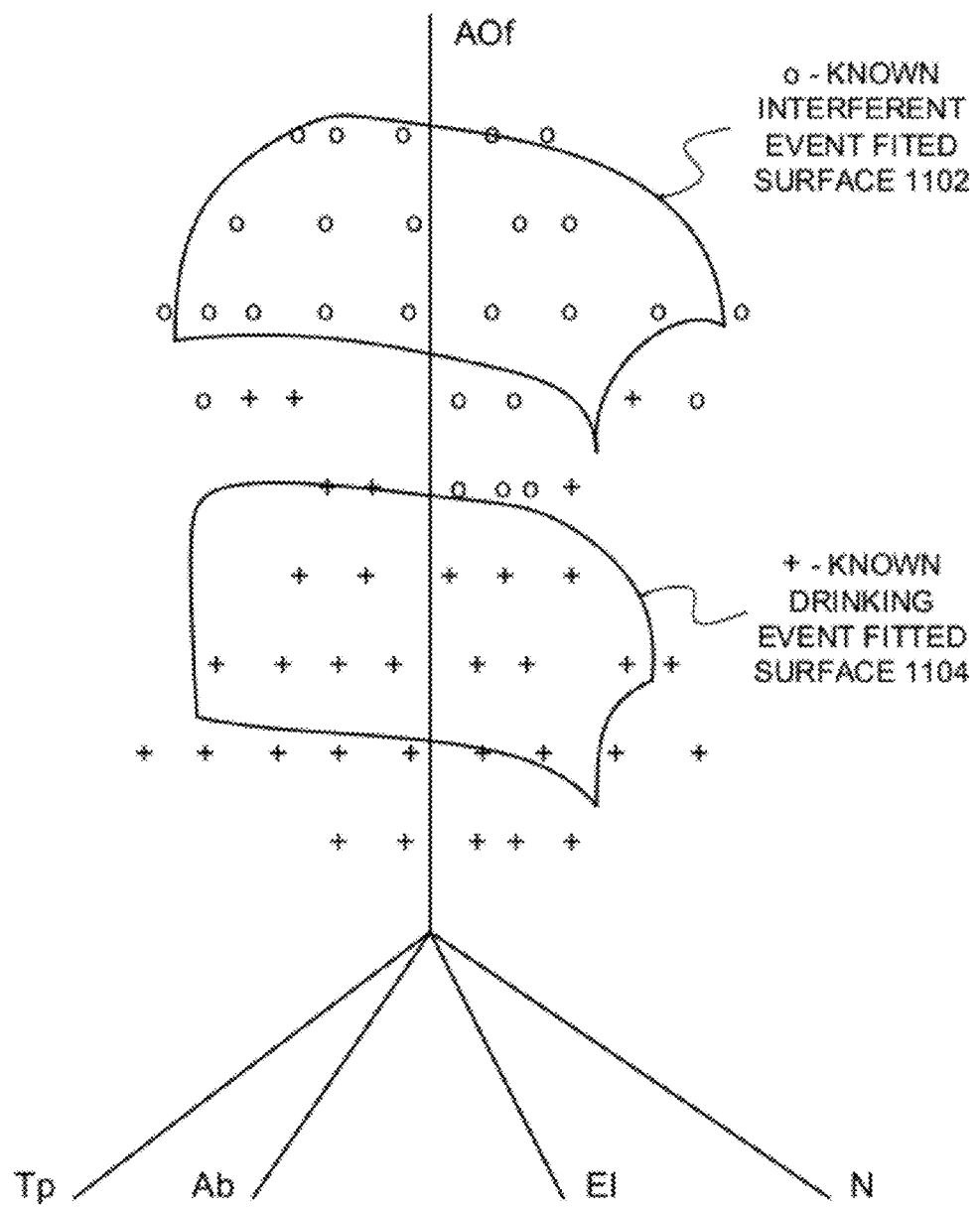
FIG. 11 shows a known interferent event fitted surface and a known drinking event fitted surface.

Offset values can be modeled as a function of these parameters using a second order response surface fit to the data group for drinking events and separately for interferent events. The terms of this type of data fit include linear, quadratic and multi-factor interaction effects. FIG. 11 shows a Known Interferent Event Fitted Surface 1102 and a Known Drinking Event Fitted Surface 1104 for each of these two event type groups.

Figure 12:
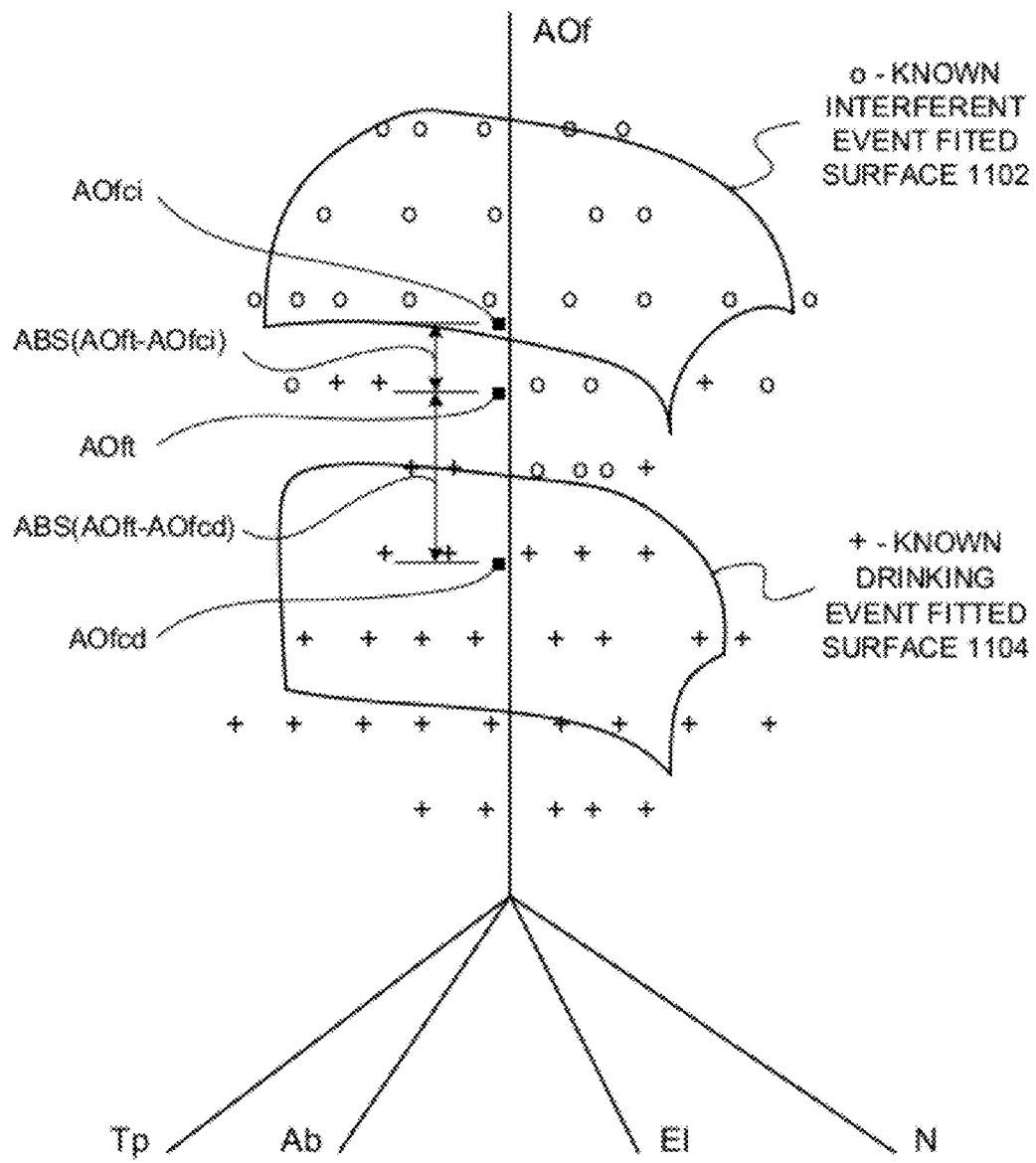
FIG. 12 shows the addition of a test event point AOft to FIG. 11 and the associated absolute value differences.

Test Event Points Relative to Interferent and Drinking Event Surfaces for Known Groups FIG. 12 shows the addition of a test event point AOft to FIG. 11 and the associated absolute value differences. For a test event with given values of the offset AOf, number of TAC reading points N, peak TAC reading Tp, and absorption rate Ab and elimination rate El, the parameter values can be substituted in each model to get estimates of the offset value for an interferent event (AOfci) and for a drinking event (AOfcd). Using these two calculated offset values and the given offset value for the test event (AOft), we can compute the distances of the test offset value to each estimated surface by comparing the absolute value of the difference between the test event offset value AOft and the calculated offset value AOfci from the interferent event equation with the absolute value of the difference between the test event offset value AOft and the calculated offset value AOfcd from the drinking event equation. Whichever group distance is the smallest indicates that the event is more likely to be classified in that group which it is closest. The absolute value differences are compared for each event relative to the known data base. If the drinking event distance is subtracted from the interferent event distance, a negative value would classify the event as an interferent and a positive value would classify it as a drinking event. A bias constant is added to this distance difference metric to force the maximum number of classifications of the known interferent group events into the proper group. That is, all or almost all of the distance differences minus the bias constant for interferent events would be zero or negative. This would maximize the percentage of the time when an event is classified to be an interferent event that it is actually an interferent event. A few drinking events will be falsely classified as interferents by this method.

Figure 13:
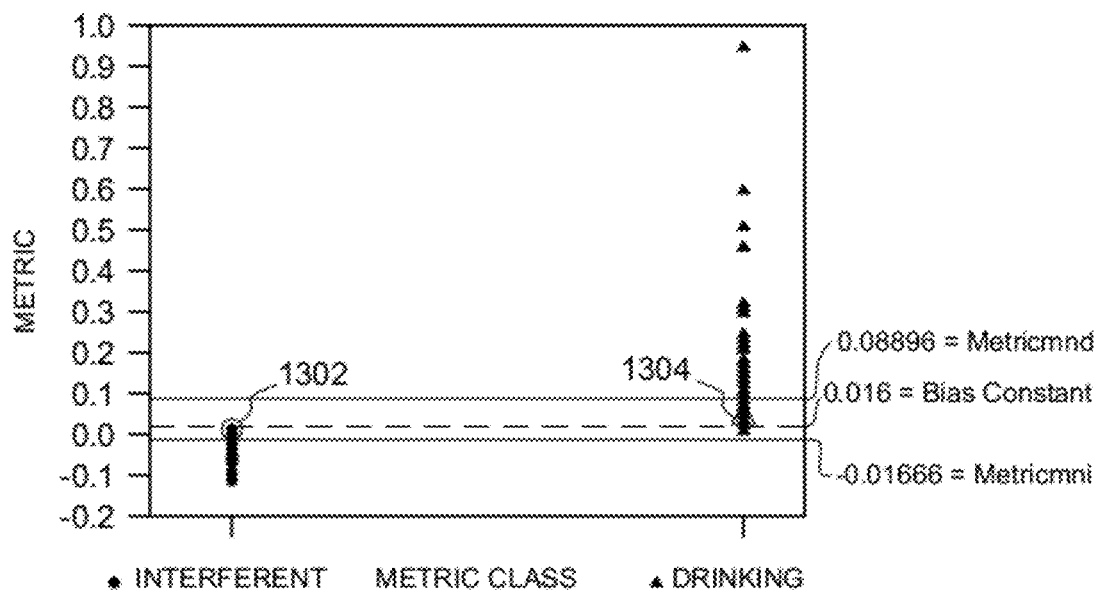
FIG. 13 shows the distributions of the distance metric values relative to the bias factor for the known interferent and drinking event groups.

Distributions of Metrics for Test Events and Known Interferent and Drinking Group Events Probability statements as to how likely test events are to be an interferent events relative to how likely they are to be drinking events are desirable. To estimate these probabilities, it is helpful to first know how well enmeshed the distance difference metric for a test event is in one or the other of the two metric populations of interferent events and drinking events from the known data base. These considerations are applied to each of three designated ranges of peak TAC, indicating regions of increasing alcohol concentration. The designated ranges are: (1) peak TAC values less than 0.08; (2) peak TAC values greater than or equal to 0.08 and less than 0.15; and (3) peak TAC values greater than or equal to 0.15. The distance difference metric values are collected into interferent and drinking groups for each of the three ranges. The average and standard deviation values of the metrics are determined for each group range. The average represents the group value about which the population values tend to cluster. FIG. 13 illustrates distributions of the distance metric values relative to the bias factor for the known interferent and drinking event groups that are in the designated range of peak TAC values less than 0.08 for Interferent Test Event Metric 1302 and for Drinking Test Event Metric 1304. The test event inputs are: AOf, Tp, Ab, El, and N for estimated AOfs, where AOfci=F1(Tp, Ab, El, N), and AOfcd=F2(Tp, Ab, El, N). Thus, Metric=ABS(AOft−AOfci)−ABS(AOft−AOfcd). If (Metric<=0.016, Metric Class=Interferent). If (Metric>0.016, Metric Class=Drinking). Similar graphs for the other two ranges are not shown.

Figure 14:
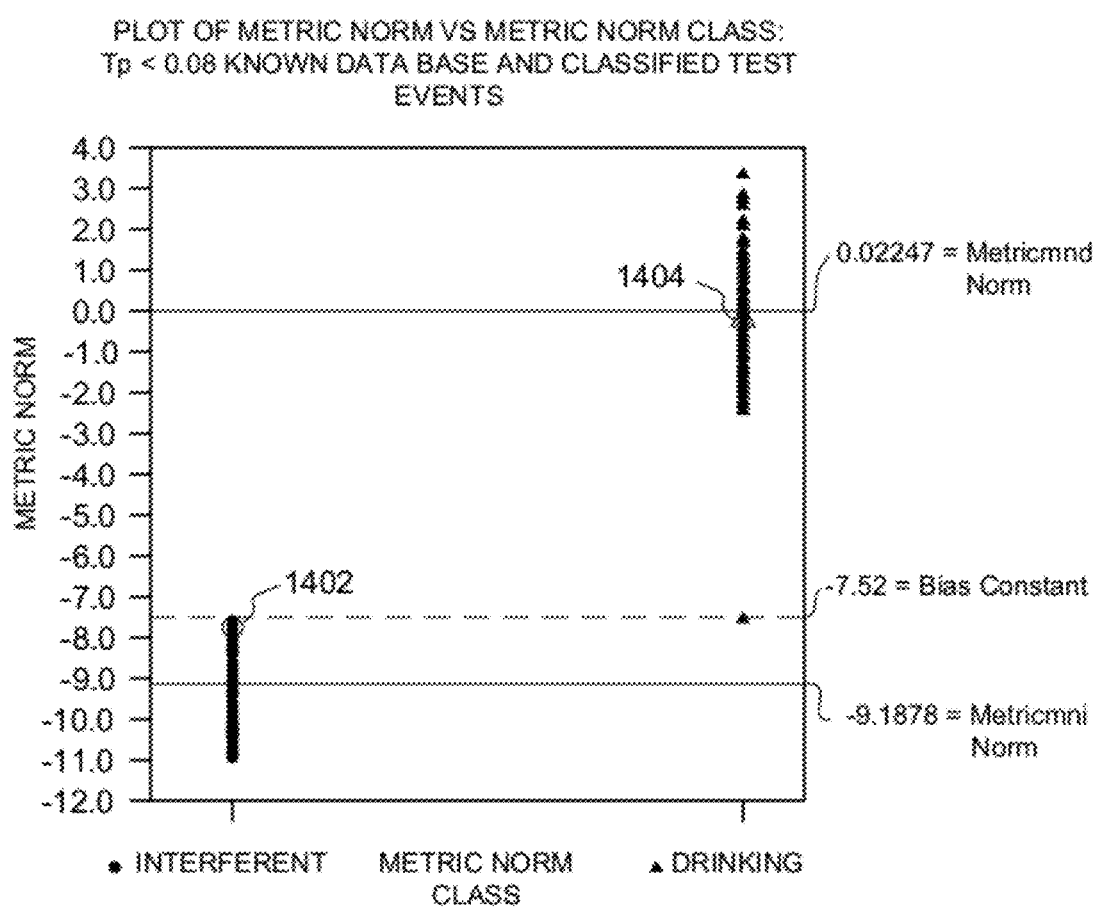
FIG. 14 shows a normal transformation made on the distance metrics for each group in FIG. 13.

Test Event Distance Metric Values Relative to Known Interferent, Drinking Event Metric Distributions FIG. 13 indicates that the interferent and drinking event populations are skewed, that is, the mean lines are nearer one end of the population rather than in the middle. The distance metric equations used in developing the group probabilities require that the distribution of values be symmetric or normal about the mean of each group. Thus, a normal transformation is made on the distance metrics for each group as shown in FIG. 14. These normalized values are then used in the distance formulas discussed below. If the known group average of the normalized values is subtracted from the normalized test metric value for the event and the difference is divided by the normalized value standard deviation for the group, the ratio being squared, the result is a measure of how far the test event metric value is from the center of either the interferent or drinking group distribution of metric values. Two times the natural log of the normalized metric group standard deviation is then added to this squared ratio difference to form the final metric as a measure of how well classified the test point metric is in the group. This metric, based on the maximum likelihood ratio of the distributions of the normalized distance difference data for the two groups, is commonly used in obtaining group probabilities, especially in the widely used MINITAB statistical analysis package under the normality assumption.

FIG. 14 includes the addition of the two test event normalized metric values for Interferent Test Event Metric 1402 and for Drinking Test Event Metric 1404 from actual tests. Notice in FIG. 14 that the normalized metric values for the known interferent and drinking event populations cluster symmetrically around the center or mean lines of the distributions, thus satisfying the normality requirements for the distance equations. The test event inputs are: AOf, Tp, Ab, El, and N for estimated AOfs, where AOfci=F1(Tp, Ab, El, N), and AOfcd=F2(Tp, Ab, El, N). Thus, Metric=ABS(AOf−AOfci)−ABS(AOf−AOfcd). If (Metric Class=Interferent, Metric Norm=F3(Metric)), and If (Metric Class=Drinking, Metric Norm=F4(Metric)) where F3 and F4 are normalized values. If (Metric Norm<=−7.52, Metric Norm Class=Interferent). If (Metric Norm>−7.52, Metric Norm Class=Drinking). Note that −7.52 is the bias factor relative to the known interferent and drinking event populations for this example.

Figure 15:
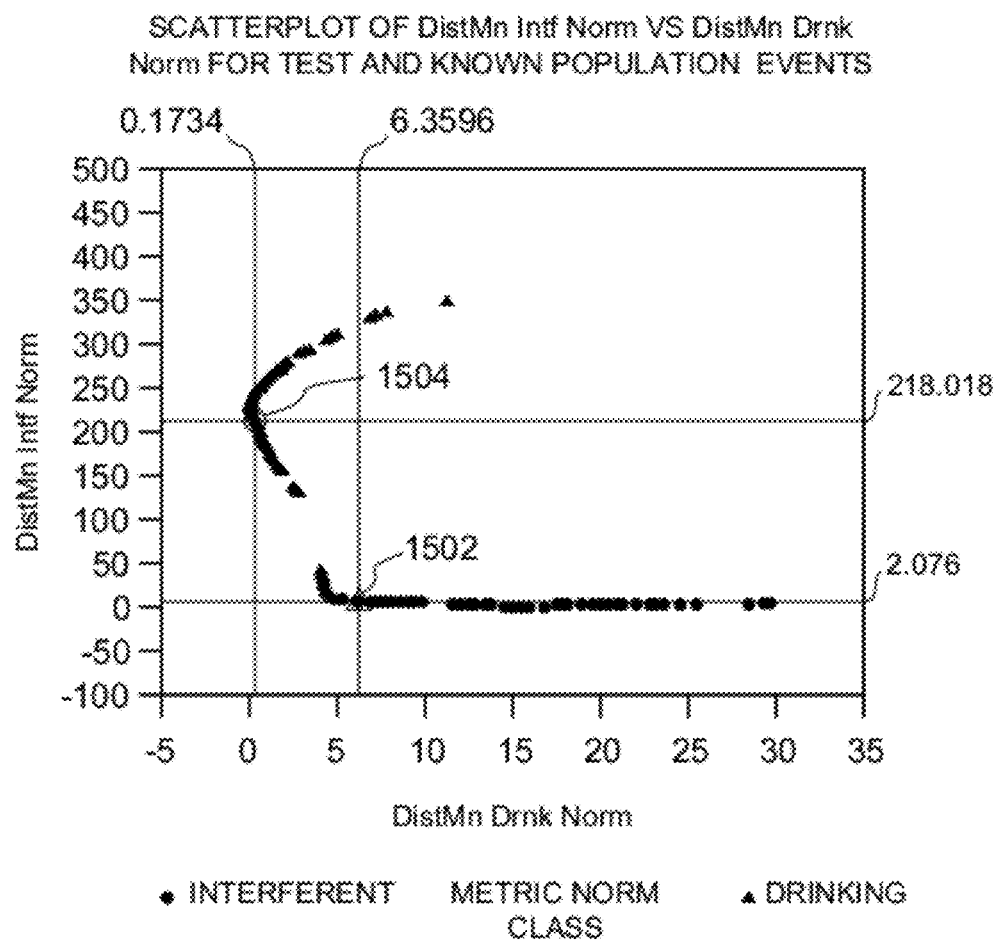
FIG. 15 shows the distance normalized metric values for the test events and interferent and drinking event known populations plotted against each other.

FIG. 15 shows the distance normalized metric values for the test events and interferent and drinking event known populations plotted against each other. The Interferent Test Event Metric 1502 and Drinking Test Event Metric 1504 are shown with their coordinate distances shown as lines. The following equations apply to FIG. 15:

DistMn Intf Norm=[(Metric Norm−Metricmni Norm)/Metricsdi Norm]**2+2*Ln(Metricsdi Norm)

DistMn Drnk Norm=[(Metric Norm−Metricmnd Norm)/Metricsdd Norm]**2+2*Ln(Metricsdd Norm)

Determination of Interferent and Drinking Event Probabilities

Figure 16:
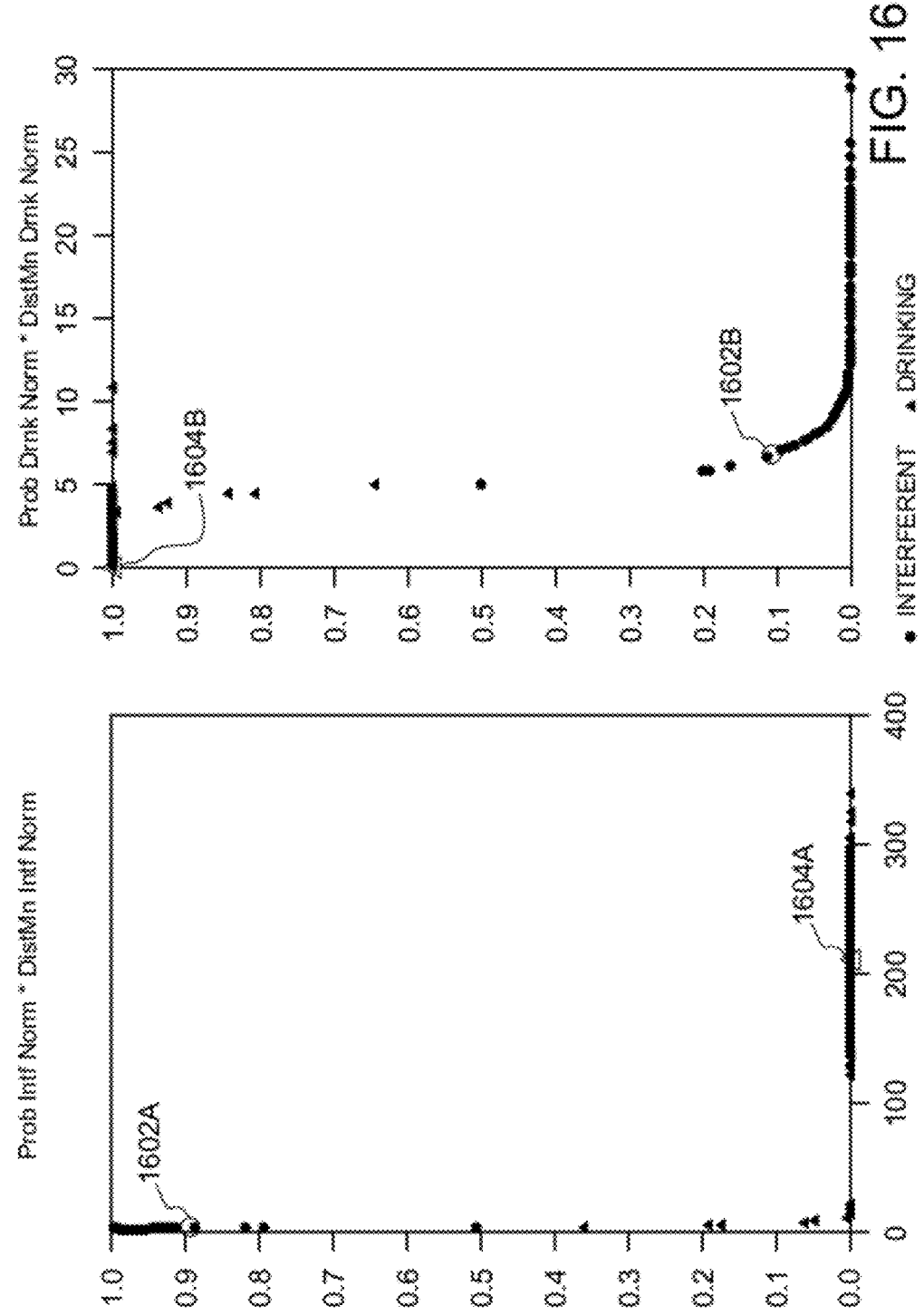
FIG. 16 shows the probability metrics versus their distances metrics from their respective populations.

These distance metric values on the normalized values are used in calculating group probabilities. A normalized probability that the event belongs in either the interferent or drinking group is one such that the two group probabilities add to one, which is the probability that the event belongs in one or the other of the two groups with certainty. The nonnormalized probability that the event belongs to one of the two groups is first defined to be the exponential of −½ times a difference, which is the group distance metric just defined, minus the minimum of the two distance metric values. One of the resulting probabilities that the event belongs in either the interferent or the drinking group will then be one and the other probability will be a value between zero and one. Since the two nonnormalized probabilities add to a value greater than one, they must be normalized to add to one. The group normalized probability is then its nonnormalized probability divided by the sum of the nonnormalized probabilities. The resulting normalized probabilities then add to one. FIG. 16 shows these probability metrics versus their distances metrics from their respective populations for Interferent Test Event Metric 1602A, 1602B and Drinking Test Event Metric 1604A, 1604B. These probabilities can then be used to measure how likely the test event is either an interferent event or a drinking event. This procedure for group probability determination is commonly used in MINITAB, the statistical package procedure cited above. This procedure provides a way of estimating the odds of whether an event is due to an interferent or whether it is due to drinking. The following equations apply to FIG. 16:

DistMn Norm Min=MIN(DistMn Intf Norm, DistMn Drnk Norm)

Prob Intf Norm NotNorm=EXP[−0.5(DistMn Intf Norm−DistMn Norm Min)]

Prob Drnk Norm NotNorm=EXP[−0.5(DistMn Drnk Norm−DistMn Norm Min)]

Prob Intf Norm=Prob Intf Norm NotNorm/(Prob Intf Norm NotNorm+Prob Drnk Norm NotNorm)

Prob Drnk Norm=Prob Drnk Norm NotNorm/(Prob Intf Norm NotNorm+Prob Drnk Norm NotNorm)

Examples of Events Likely to be Interferent or Drinking

As noted before, the inputs to a program evaluating these probabilities are simply the percent offset/100 measure AOf, the number of TAC readings N, the absorption rate Ab, the elimination rate El, and the peak TAC Tp values for the test event. FIGS. 13, 14, 15, and 16 show the evaluation process for the interferent test and drinking test events. For the Interferent Test Event Metric 1302, 1402, 1502, 1602A, 1602B example, the percent offset values for the interferent and drinking event surface estimates are AOfci=F1(Tp,Ab,El,N)=F1(0.034,0.0085,0.0076,6)=1.07989; and AOfcd=F2(Tp,Ab,El,N)=F2(0.034,0.0085,0.0076,6)=1.01432. The distance metric value for the observed AOft=1.04 is then Metric=ABS(AOft−AOfci)−ABS(AOft−AOfcd)=ABS(1.04−1.07989)−ABS(1.04−1.01432)=0.01421 shown by Interferent Test Event Metric 1302 in FIG. 13. This event is shown normalized in Interferent Test Event Metric 1402 in FIG. 14 with Metric norm=−7.7824 for interferent events. Using the interferent population statistics for FIG. 14, the distance of the test event metric from the interferent population is defined in FIG. 15 as DistMn Intf Norm=[(Metric norm−Metricmni norm)/Metricsdi norm]**2+2*Ln(Metricsdi norm)=[(−7.7824+9.1878)/0.954]**2+2*Ln(0.954)=2.076. Using the drinking population statistics for FIG. 14, the distance of the test event metric from the drinking population is defined in FIG. 15 as DistMn Drnk Norm=[(Metric norm−Metricmnd norm)/Metricsdd norm]**2+2*Ln(Metricsdd norm)=[(−2.56313−0.02247)/1.03011]**2+2*Ln(1.03011)=6.3596 with Metric norm as −2.56313 for drinking events. Interferent Test Event Metric 1502 is located at the intersection of the two lines defining these two values in FIG. 15.

FIG. 16 defines the minimum of these two distance metric values to be DistMn Norm Min=MIN(DistMn Intf Norm, DistMn Drnk Norm)=MIN(2.076, 6.3596)=2.076. The nonnormalized probability that the test event is an interferent as defined in FIG. 16 is Prob Intf Norm NotNorm=EXP[−0.5 (DistMn Intf Norm−DistMn Norm Min)]=EXP[−0.5(2.076− 2.076)]=1. The nonnormalized probability that the test event is a drinking event as defined in FIG. 16 is Prob Drnk Norm NotNorm=EXP[−0.5(DistMn Drnk Norm−DistMn Norm Min)]=EXP[−0.5(6.3596−2.076)]=0.117. The normalized probability that the event is an interferent is given in FIG. 16 as Prob Intf Norm=ProbIntf Norm NotNorm/(ProbIntf Norm NotNorm+ProbDrnk Norm NotNorm)=1/(1+0.117)=0.895. This value is located at Test Event Metric 1602A in FIG. 16 on the Prob Intf Norm*DistMn Intf Norm graph. The normalized probability that the event is a drinking event is given in FIG. 16 as Prob Drnk Norm=ProbDrnk Norm NotNorm/(ProbIntf Norm NotNorm+ProbDrnk Norm NotNorm)=0.117/(1+ 0.117)=0.105. This value is located at Test Event Metric 1602B in FIG. 16 on the Prob Drnk Norm*DistMn Drnk Norm graph. Comparing these two values and noting their event positions 1602A and 1602B on the two graphs in FIG. 16, it is noted that the event is more likely to be an interferent event.

For the Drinking Test Event Metric 1304, 1404, 1504, 1604A, 1604B example, the percent offsets values for the interferent and drinking event surface estimates are AOfci=F1 (Tp,Ab,El,N)=F1(0.119,0.0298,0.0092,18)=0.9429, AOfcd=F2(Tp,Ab,El,N)=F2(0.119,0.0298,0.0092,18)= 1.02316. The average percent offset value/100 for the observed AOft=1.0084. Using these values and the same procedure as for the interferent test event and utilizing FIGS. 13, 14, 15, and 16 and equations, we find that Prob Intf Norm=0.000 and Prob Drnk Norm=1.000. These values and the graphs for the drinking test event on FIG. 16 indicate that it is most likely a drinking event. By establishing a desired probability of a higher or lower value, more or less sensitivity can be achieved.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. It will be understood by those skilled in the art that many changes in construction and widely differing embodiments and applications will suggest themselves without departing from the scope of the disclosed subject matter.

What is claimed is:

1. A method for detecting an environmental interferent in an event monitored by a transdermal alcohol monitor adapted to be worn by a subject, the method comprising the steps of:
   (a) calculating an average baseline value (ABV) for the transdermal alcohol monitor;
   (b) calculating a maximum allowable average baseline value (MAABV) for the transdermal alcohol monitor based upon the ABV;
   (c) calculating an event average baseline value (EABV) for the event monitored by the transdermal alcohol monitor; and
   (d) identifying the event as an interferent event if the EABV is greater than or equal to the MAABV.

2. The method according to claim 1 further comprising the step of:
   identifying the event as a drinking event if the EABV is less than the MAABV.

3. The method according to claim 1 wherein step (a) further comprises the steps of:
   retrieving a plurality of baseline value readings stored since the transdermal alcohol monitor was attached to the subject and up to the event monitored by the transdermal alcohol monitor, wherein the plurality of baseline value readings stored are derived from transdermal alcohol concentration (TAC) readings that measure less than a predetermined minimum % w/v; and
   averaging the plurality of baseline value readings stored to determine the ABV.

4. The method according to claim 3 wherein the predetermined minimum % w/v is about 0.001% w/v.

5. The method according to claim 3 wherein said method further comprises the steps of:
   for each TAC reading, taking one or more readings from an alcohol sensor in the transdermal alcohol monitor prior to an air sample being introduced into the alcohol sensor of the transdermal alcohol monitor; and
   averaging the one or more alcohol sensor readings to determine a baseline value for each TAC reading.

6. The method according to claim 1 wherein step (b) further comprises the step of:
   calculating the MAABV according to a following formula:

$$MAABV = ((1.01 + (0.0033 *\text{\# of TAC Readings In The Event})) * 100) * ABV$$

wherein the # of TAC Readings In The Event is a number of TAC readings that measured more than a predetermined maximum % w/v.

7. The method according to claim 6 wherein step (c) further comprises the steps of:
   averaging a number of TAC readings in the event that measured over the predetermined maximum % w/v to calculate the EABV.

8. The method according to claim 7 wherein the predetermined maximum % w/v is about 0.02% w/v.

9. The method according to claim 1 wherein the ABV, MAABV, and EABV are calculated from one of a electric current output of the transdermal alcohol monitor and a voltage of the electric current output from the transdermal alcohol monitor.

10. A system for detecting an environmental interferent in an event, the system comprising:
    a transdermal alcohol monitor adapted to be worn by a subject, wherein the transdermal alcohol monitor takes a plurality of transdermal alcohol concentration (TAC) readings over a period of time;
    a monitoring network in communication with the transdermal alcohol monitor, wherein the transdermal alcohol monitor sends the plurality of TAC readings to the monitoring network; and
    a computing device that receives the plurality of TAC readings, wherein the computing device calculates:
        an average baseline value (ABV) for the transdermal alcohol monitor worn by the subject;
        a maximum allowable average baseline value (MAABV) for the transdermal alcohol monitor based upon the ABV; and
        an event average baseline value (EABV) for the event monitored by the transdermal alcohol monitor;
    wherein the computing device compares the EABV to the MAABV to determine if the event is an interferent event.

11. The system according to claim 10 wherein if the EABV is greater than or equal to the MAABV, the computing device identifies the event as an interferent event.

12. The system according to claim 10 wherein if the EABV is less than the MAABV, the computing device identifies the event as a drinking event.

13. The system according to claim 10 further comprising:
a storage device in communication with the computing device, wherein a plurality of baseline value readings since the transdermal alcohol monitor was attached to the subject, and up to the event monitored by the transdermal alcohol monitor, are stored, wherein the plurality of baseline value readings stored are derived from TAC readings that measured less than a predetermined minimum % w/v, and further wherein the computing device averages the plurality of baseline value readings stored to determine the ABV.

14. The system according to claim 13 wherein the predetermined minimum % w/v is about 0.001% w/v.

15. The system according to claim 10 wherein the transdermal alcohol monitor further comprises:
an alcohol sensor which takes TAC readings from an air sample introduced to the alcohol sensor.

16. The system according to claim 15 wherein for each TAC reading, one or more alcohol sensor readings are taken prior to an air sample being introduced into the transdermal alcohol monitor, and further wherein the one or more alcohol sensor readings are averaged by the computing device to determine a baseline value for each TAC reading.

17. The system according to claim 15 wherein the alcohol sensor is selected from the group consisting of a fuel cell sensor and a solid state sensor.

18. The system according to claim 10 wherein the computing device calculates the MAABV according to a following formula:

$$MAABV=((1.01+(0.0033*\text{\# of TAC Readings In The Event}))*100)*ABV$$

wherein the # of TAC Readings In The Event is a number of TAC readings that measured more than a predetermined maximum % w/v.

19. The system according to claim 18 wherein the computing device averages a number of TAC readings in the event that measured over the predetermined maximum % w/v to calculate the EABV.

20. The system according to claim 19 wherein the predetermined maximum % w/v is about 0.02% w/v.

21. The system according to claim 10 further comprising:
a modem;
a first communication channel between the transdermal alcohol monitor and the modem; and
a second communication channel between the modem and the monitoring network;
wherein the TAC readings from the transdermal alcohol monitor are sent over the first communication channel to the modem, and the TAC readings are sent from the modem over the second communication channel to the monitoring network.

22. The system according to claim 21 wherein the computing device is located in the monitoring network.

23. The system according to claim 10 wherein the ABV, MAABV, and EABV are calculated from one of a current output of the transdermal alcohol monitor and a voltage of the current output from the transdermal alcohol monitor.

24. A method for detecting an environmental interferent in a transdermal alcohol concentration (TAC) reading taken by a transdermal alcohol monitor, the method comprising the steps of:

(a) for each TAC reading, taking one or more alcohol sensor readings prior to an air sample being introduced into an alcohol sensor of the transdermal alcohol monitor;
(b) averaging the one or more alcohol sensor readings to determine a baseline value for each TAC reading;
(c) storing the baseline value for each TAC reading;
(d) repeating steps (a) through (c) for a plurality of TAC readings;
(e) for each TAC reading that measured less than a predetermined minimum value, averaging the baseline values stored to determine an average baseline value for the transdermal alcohol monitor;
(f) multiplying the average baseline value by a predetermined maximum value to determine a maximum value for the transdermal alcohol monitor;
(g) taking a next TAC reading and determining a baseline value for the next TAC reading; and
(h) if the baseline value for the next TAC reading is greater than or equal to the maximum value for the transdermal alcohol monitor, determining that the next TAC reading was taken in a presence of the environmental interferent.

25. The method according to claim 24 wherein if the baseline value for the next TAC reading is less than the maximum value for the transdermal alcohol monitor, determining that the next TAC reading was taken in an absence of the environmental interferent.

26. The method according to claim 24 wherein said predetermined minimum value is about 0.001% w/v and said predetermined maximum value is about 0.02% w/v.

27. The method according to claim 24 further comprising the step of:
if the next TAC reading is greater than or equal to the maximum value for the transdermal alcohol monitor, disregarding the next TAC reading in determining a drinking event.

28. The method according to claim 24 further comprising the step of:
if the next TAC reading is less than the maximum value for the transdermal alcohol monitor, using the next TAC reading in determining a drinking event.

29. A method for detecting an environmental interferent in an event monitored by a transdermal alcohol monitor adapted to be worn by a subject, the method comprising the steps of:
(a) determining a set of metrics for known event type groups taken by the transdermal alcohol monitor, wherein the known event type groups are a drinking events type group and an interferent events type group;
(b) determining a same set of metrics from a test event;
(c) comparing the set of metrics from the test event to the set of metrics from the known event type groups;
(d) calculating a probability of the test event being an interferent event; and
(e) if the calculated probability is greater than or equal to a predetermined value, categorizing the test event as an interferent event.

30. The method according to claim 29 further comprising the steps of:
categorizing the test event as a drinking event if the calculated probability is less than the predetermined value.

31. The method according to claim 29 further comprising the step of:
determining a first probability of the test event being in the interferent event group;
determining a second probability of the test event being in the drinking event group; and categorizing the test event as an interferent event if the first probability is greater than the second probability.

32. The method according to claim 31 further comprising the step of:
categorizing the test event as a drinking event if the first probability is less than the second probability.

33. The method according to claim 29 further comprising the step of:
normalizing the set of metrics from the test event.

34. The method according to claim 33 wherein step (a) further comprises the steps of:
(a1) determining a response surface equation for the drinking events type group;
(a2) determining a response surface equation for the interferent events type group;
(a3) determining an absolute value of a difference between an each known group event offset value from an each group equation computed offset value based upon the response surface equation for the drinking events type group;
(a4) determining an absolute value of a difference between an each known group event offset value from an each group equation computed offset value based upon the response surface equation for the interferent events type group; and
(a5) normalizing the differences from steps (a3) and (a4).

35. The method according to claim 34 further comprising the step of:
determining the response surface equations for the drinking events type group and the interferent events type group by using the offset value as a function of the observed event number of transdermal alcohol concentration (TAC) readings, an absorption rate of the subject's skin, an elimination rate of the subject's skin, and a peak TAC reading.

36. The method according to claim 35 further comprising the steps of:
calculating the offset values by utilizing means and standard deviations of the normalized offset values for the drinking events type group and the interferent events type group and the normalized offset value of the test event.

* * * * *